United States Patent [19]
Pascal et al.

[11] Patent Number: 5,972,927
[45] Date of Patent: Oct. 26, 1999

[54] DIAZEPINOINDOLES AS PHOSPHODIESTERASE 4 INHIBITORS

[75] Inventors: Yves Pascal, Rueil-Malmaison; Henry Jacobelli, Parray-Vieille-Poste, both of France; Alain Calvet, Ann Arbor, Mich.; Adrian Payne, Westerham, United Kingdom; Svein G. Dahl, Gif-sur-Yvette, France

[73] Assignee: Jouveinal, Fresnes, France

[21] Appl. No.: 08/952,891

[22] PCT Filed: Mar. 27, 1997

[86] PCT No.: PCT/FR97/00557

§ 371 Date: Apr. 7, 1998

§ 102(e) Date: Apr. 7, 1998

[87] PCT Pub. No.: WO97/36905

PCT Pub. Date: Oct. 9, 1997

[30] Foreign Application Priority Data

Mar. 29, 1996 [FR] France ................. 96 04013

[51] Int. Cl.⁶ ............ C07D 487/06; C07D 519/00; A61K 31/55
[52] U.S. Cl. ............ 514/211; 540/496
[58] Field of Search ............ 540/496; 514/211

[56] References Cited

U.S. PATENT DOCUMENTS 5,082,937  1/1992  Calvet et al. ............ 540/496
5,852,190  12/1998  Pascal et al. ............ 540/496

FOREIGN PATENT DOCUMENTS 265 734      5/1988  European Pat. Off. .
WO 96/11690  4/1996  WIPO .

*Primary Examiner*—Mukund J. Shah
*Assistant Examiner*—Bruck Kifle
*Attorney, Agent, or Firm*—Todd M. Crissey

[57] ABSTRACT

Diazepinoindoles of formula (I),

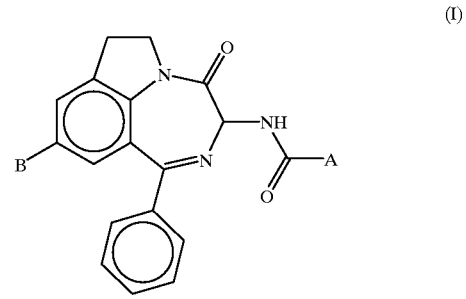

wherein A is mono- to trisubstituted aryl or heteroaryl, and B is an —$OR_1$ or —$NR_2R_3$ group where $R_1$, $R_2$ and $R_3$ are particularly hydrogen, and racemic forms, enantiomers and pharmaceutically acceptable salts thereof, as phosphodiesterase IV inhibitors, are disclosed.

23 Claims, No Drawings

DIAZEPINOINDOLES AS PHOSPHODIESTERASE 4 INHIBITORS

FIELD OF THE INVENTION

The present invention relates to novel [1,4]diazepino[6,7,1-hi]indoles which are useful for the preparation of medicinal products which make it possible to treat complaints that fall within the scope of a therapy by a phosphodiesterase 4 inhibitor. These medicinal products are useful in particular as antiinflammatory agents, antiallergic agents, bronchodilators or antiasthmatic agents, and are devoid of secondary effects on the heart or digestive system.

TECHNICAL BACKGROUND OF THE INVENTION

In contrast to the properties disclosed by the present invention, the prior art is based on is [1,4]diazepino[6,7,1-hi]indoles for which antagonist properties with respect to cholecystokinin (CCK) and/or gastrin are described, and which are proposed for complaints of the digestive tract: stomach, intestine, pancreas and gall bladder, and in particular eating disorders.

Thus, European patent application No. 340,064 describes compounds of formula:

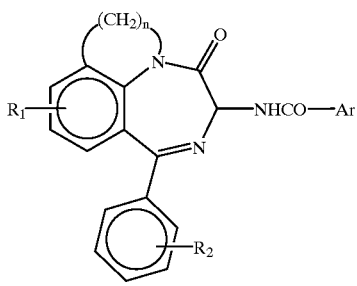

in which $R_1$ and $R_2$ are hydrogen or halogen, Ar is indolyl or phenyl and n is 2 or 3. These compounds are peripheral cholecystokinin antagonists ($CCK_A$).

European patent application no. 360,079 describes peripheral and/or central CCK-antagonist compounds of formula:

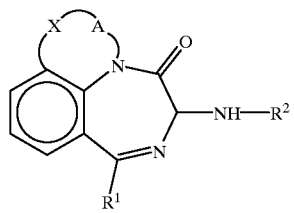

in which $R^1$ is optionally substituted aryl, X is oxygen or methylene optionally substituted with a lower alkyl radical, A is a bond or lower alkylene which may have one or more lower alkyl groups, and $R^2$ is hydrogen or acyl. Unpublished French patent application No. FR 94/12282 describes the application of diazepinoindole derivatives of formula

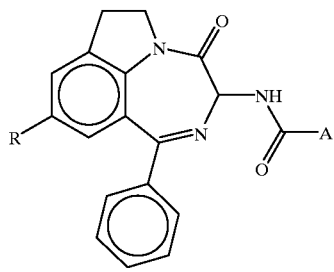

in which R is hydrogen, lower alkyl or lower alkoxy, and A is an optionally substituted aromatic ring, some of which derivatives are novel, for the preparation of medicinal products intended for the treatment of complaints that fall within the scope of a phosphodiesterase 4 inhibitor.

As regards the inhibition of phosphodiesterases, it is recalled that adenosine 3', 5'-cyclic monophosphate (cAMP) is a ubiquitous intracellular second messenger, which is intermediate between a first messenger (hormone, neurotransmitter or autacoid) and the functional responses of the cell: the first messenger stimulates the enzyme responsible for the synthesis of cAMP; depending on the cells under consideration, the cAMP then becomes involved in a great many functions: metabolic, contractile or secretory.

The effects of cAMP come to an end when it is degraded by cyclic nucleotide phosphodiesterases, intracellular enzymes which catalyze its hydrolysis into inactive adenosine 5'-monophosphate.

In mammals, it is possible to distinguish at least five major classes of cyclic nucleotide phosphodiesterase (PDE) numbered from 1 to 5 according to their structure, their kinetic behavior, their substrate specificity or their sensitivity to effectors (Beavo J. A. et al. (1990) Trends Pharmacol. Sci. 11, 150–155. Beavo J. A. et al. (1994) Molecular Pharmacol. 46, 399–405). The PDEs 4 are specific for cAMP.

Nonspecific phosphodiesterase inhibitor compounds are known, these inhibiting several classes of enzymes. This is the case for certain methylxanthines such as theophylline. These compounds have a low therapeutic index, in particular on account of their action on types of PDE present in cells other than the target cells. In contrast, certain classes of PDE can be selectively inhibited by various pharmacological agents: hydrolysis of the cyclic nucleotides is slowed down and thus their concentration increases only in those cells containing the type of PDE which is sensitive to the inhibitor.

Particular interest is evident for phosphodiesterases 4 (PDEs 4), which have been identified in many tissues including the central nervous system, the heart, vascular endothelium, vascular smooth muscle and that of the airways and the myeloid and lymphoid lines.

An increase in cAMP in the cells involved in inflammation inhibits their activation: inhibition of the synthesis and of the release of mediators at the level of mastocytes, monocytes, eosinophil and basophil polymorphonuclear leukocytes, inhibition of chemotaxis and of the degranulation of neutrophil and eosinophil polymorphonuclear leukocytes and inhibition of lymphocyte division and differentiation.

Cytokines, in particular TNF and interleukins, produced by various types of leukocyte such as T lymphocytes and eosinophil polymorphonuclear leukocytes, play an important role in the triggering of inflammatory manifestations, in particular in response to stimulation by an allergen in the respiratory pathways.

Moreover, cAMP reduces the tonus of smooth muscle fibers in the airways; PDE 4 inhibitors bring about bronchial relaxation.

It is thus possible to expect that PDE 4-selective inhibitors will possess a therapeutic activity as antiinflammatory, antiallergic and bronchodilatory medicinal products, and in the treatment of asthma, in which infiltration of the airways by inflammatory cells and bronchoconstriction are observed.

Theophylline has been very widely used for a long time in the treatment of asthma, and, although its mechanism of action is complex, the inhibition of PDE contributes to its action, but also to certain undesirable effects such as nausea and headaches.

In recent years, extensive research has been carried out in order to obtain and develop powerful PDE 4 inhibitors. This proves to be difficult on account of the fact that many potential PDE 4 inhibitors are not devoid of activity on the phosphodiesterases of other classes.

At present, the lack of selectivity of PDE 4 inhibitors thus represents a considerable problem, given the extent of the functions regulated by cAMP, the said problem still needing to be considered as poorly resolved or unresolved. There is thus a need for powerful and selective PDE 4 inhibitors, that is to say inhibitors which have no action with respect to the PDEs belonging to other classes.

Thus, rolipram (INN), a pyrrolidone derivative first synthesized in 1975, is considered to be representative of PDE 4-specific inhibitors. Many compounds related to rolipram have been synthesized with a view to their use as PDE 4 inhibitors. In vitro, rolipram inhibits the activity of inflammatory cells in rodents: inhibition of the synthesis of mediators by mastocytes, eosinophil and basophil polymorphonuclear leukocytes and monocytes; inhibition of chemotaxis and of the degranulation of polymorphonuclear leukocytes. Rolipram has been proposed as an antidepressant; however, its use is accompanied by undesirable effects of the type involving nausea and vomiting.

SUMMARY OF THE INVENTION

Now, overcoming the difficulties reported in the prior art, novel [1,4]diazepino[6,7,1-hi]indole derivatives have now been found, which are powerful PDE 4 inhibitors at concentrations at which they have little or no action on the other classes of PDE.

The invention relates to the diazepinoindoles of formula (I)

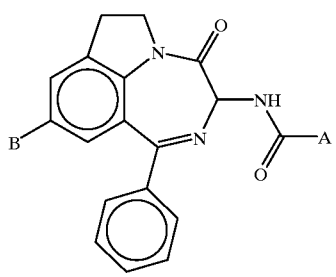

in which:
A is aryl or nitrogen-containing heteroaryl, each optionally being substituted with one to three groups chosen independently from halogen, lower alkyl, lower haloalkyl, lower alkoxy, cycloalkyloxy, amino and lower alkylcarbonylamino or alkyloxycarbonylamino;
B is a hydroxyl or amino radical, itself optionally substituted, a process for their preparation and their application to the production of medicinal products intended to treat complaints that fall within the scope of a therapy by the inhibition of PDE 4.

DETAILED DESCRIPTION OF THE INVENTION

The invention is directed towards the diazepinoindoles of formula (I)

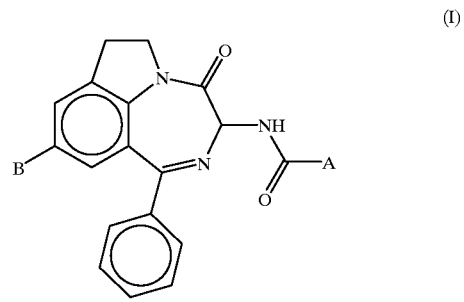

in which:
A is aryl or nitrogen-containing heteroaryl, each optionally being substituted with one to three groups chosen independently from halogen, lower alkyl, lower haloalkyl, lower alkoxy, cycloalkyloxy, amino and lower alkylcarbonylamino or alkyloxycarbonylamino;

B is:
1°) —OR$_1$, R$_1$ being —H or R$_4$,
2°) —NR$_2$R$_3$, R$_2$ being —C(NH)NH$_2$ and R$_3$ being —H,
3°) —NR$_2$R$_3$, R$_2$ being R$_4$ and R$_3$ being —H,
4°) —NR$_2$R$_3$, R$_2$ and R$_3$ independently being —H or lower alkyl, or
5°) —N—R—R, R$_2$ and R$_3$ forming, together with the nitrogen atom to which they are attached, a saturated five- to seven-membered heterocycle which may comprise, as second hetero atom not attached directly to the nitrogen atom, an oxygen, a sulfur or a nitrogen;

R$_4$ is:
1°) —CH$_2$—CO$_2$H,
2°) —CO—(CH$_2$)$_p$—CO$_2$H,
3°) —CO—A, where A has the definition indicated above,
4°) —CO—CH=CH—CO$_2$H,
5°) —CO—(CH$_2$)n—CH$_3$, n being an integer equal to or greater than 0 and less than or equal to 18,
6°) —CO—(CH$_2$—O—CH$_2$)$_p$—CH$_2$—O—CH3,
7°) —CO—(CH$_2$—O—CH$_2$)$_p$—CO$_2$H,
8°) —(CH$_2$)$_p$—NR$_5$R$_6$, R$_5$ and R$_6$ independently being -H or lower alkyl, or
9°) —(CH$_2$)p—NR$_5$R$_6$, R$_5$ and R$_6$ forming, together with the nitrogen atom to which they are attached, a saturated five- to seven-membered heterocycle which may comprise, as second hetero atom not attached directly to the nitrogen atom, an oxygen, a sulfur or a nitrogen;

p is an integer equal to 2, 3 or 4;
the racemic forms and isomers thereof, in particular those of configuration determined by carbon 3 of the diazepinoindol-4-one ring,
as well as the pharmaceutically acceptable salts thereof.
In the following and in the foregoing text:

aryl is understood to refer to phenyl or naphthyl;

nitrogen-containing heteroaryl is understood to refer to a non-saturated monocycle or polycycle containing at least one nitrogen atom and, preferably, five- to seven-membered heteromonocycles containing from 1 to 4 nitrogen atoms, or alternatively non-saturated condensed heterocycles containing from 1 to 4 nitrogen atoms, optionally methylated or ethylated on a positively charged nitrogen atom;

halogen is understood to refer to fluorine, chlorine, bromine or iodine;

as regards radicals comprising an alkyl sequence, lower is understood to mean that the alkyl is linear or branched and contains from one to four carbon atoms, or alternatively represents the cyclopropylmethyl radical;

cycloalkyl is understood to refer to cyclopropyl, cyclobutyl, cyclopentyl or cyclohexyl groups;

haloalkyl is understood to refer to a mono-, di- or trihaloalkyl.

A review of the salts acceptable in pharmacy will be found in J. Pharm. Sci., 1977, 66, 1–19. The expression pharmacologically acceptable salt of a compound of formula (I) having a basic part should be understood to refer to the addition salts of the compounds of formula (I) which may be formed from non-toxic inorganic or organic acids such as, for example, hydrobromic, hydrochloric, sulfuric, phosphoric, nitric, acetic, succinic, tartaric, citric, maleic, hydroxymaleic, benzoic, fumaric, toluenesulfonic and isethionic acid salts, and the like. The various quaternary ammonium salts of the derivatives (I) are also included in this category of compounds of the invention. In addition, the expression pharmacologically acceptable salt of a compound of formula (I) having an acidic part is understood to refer to the usual salts of the compounds of formula (I) which may be formed from non-toxic inorganic or organic bases such as, for example, the hydroxides of alkali metals and alkaline-earth metals (sodium, potassium, magnesium and calcium), amines (dibenzylethylenediamine, trimethylamine, piperidine, pyrrolidine, benzylamine and the like) or alternatively quaternary ammonium hydroxides such as tetramethylammonium hydroxide.

The diazepinoindoles of formula (I) in which the asymmetric carbon atom in an alpha position relative to the "3-one" carbonyl of the diazepine ring possesses the (R) absolute configuration according to the Cahn-Ingold-Prelog rule are generally preferred.

A group of compounds (I) in which B is $OR_1$ or $NR_2R_3$ with $R_1$, $R_2$ and $R_3$ representing hydrogen is preferred.

Another set of products (I) consisting of those in which A is aryl substituted with 1 to 3 groups independently chosen from halogen, amino, lower alkyloxycarbonylamino or alkoxy is advantageously preferred, as well as the set of products (I) in which A is monocyclic heteroaryl comprising from 1 to 2 nitrogen atoms or bicyclic heteroaryl comprising from 1 to 4 nitrogen atoms.

More particularly, the following compounds (I):

(3R)-isoquinoline-3-carboxylic acid (9-hydroxy-4-oxo-1-phenyl-3,4,6,7-tetrahydro[1,4]diazepino[6,7,1-hi]indol-3-yl)amide (3R)-4-t-butyloxycarbonylamino-N-(9-amino-4-oxo-1-phenyl-3,4,6,7-tetrahydro[1,4]diazepino[6,7,1-hi]indol-3-yl)benzamide (3R)-4-amino-N-(9-amino-4-oxo-1-phenyl-3,4,6,7-tetrahydro[1,4]diazepino[6,7,1-hi]indol-3-yl)-3,5-dichlorobenzamide (3R)-4-amino-N-(9-amino-4-oxo-1-phenyl-3,4,6,7-tetrahydro[1,4]diazepino[6,7,1-hi]indol-3-yl)-5-chloro-2-methoxybenzamide (3R)-N-(9-amino-4-oxo-1-phenyl-3,4,6,7-tetrahydro-[1,4]diazepino[6,7,1-hi]indol-3-yl)isonicotinamide (3R)-3-t-butyloxycarbonylamino-N-(9-amino-4-oxo-1-phenyl-3,4,6,7-tetrahydro[1,4]diazepino[6,7,1-hi]indol-3-yl)isonicotinamide, and its addition salt with sulfuric acid, (3R)-isoquinoline-3-carboxylic acid (9-amino-4-oxo-1-phenyl-3,4,6,7-tetrahydro[1,4]diazepino[6,7,1-hi]indol-3-yl)amide (3R)-quinoline-3-carboxylic acid (9-amino-4-oxo-1-phenyl-3,4,6,7-tetrahydro[1,4]diazepino[6,7,1-hi]indol-3-yl)amide (3R)-4,7-dimethylpyrazolo[5,1-c][1,2,4]triazine-3-carboxylic acid (9-amino-4-oxo-1-phenyl-3,4,6,7-tetrahydro[1,4]diazepino[6,7,1-hi]indol-3-yl)amide, (3R)-4-amino-3,5-dichloro-N-(9-dimethylamino-4-oxo-1-phenyl-3,4,6,7-tetrahydro[1,4]diazepino[6,7,1-hi]indol-3-yl)benzamide, (3R)N-(9-amino-4-oxo-1-phenyl-3,4,6,7-tetrahydro-[1,4]diazepino[6,7,1-hi]indol-3-yl)-2-benzofuranecarboxamide, (3R)4,7-dimethyl-pyrazolo[5,1-c][1,2,4]triazine-3-carboxylic acid[4-oxo-1-phenyl-9-(pyrrolidin-1-yl)-3,4,6,7-tetrahydro-[1,4]diazepino[6,7,1-hi]indol-3-yl]-amide, are preferred.

Scheme 1

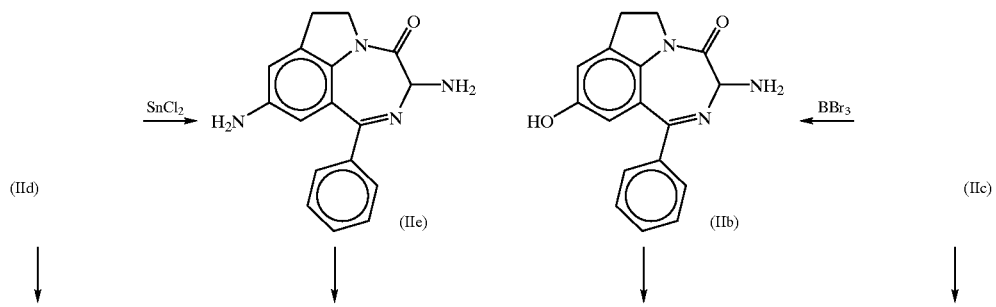

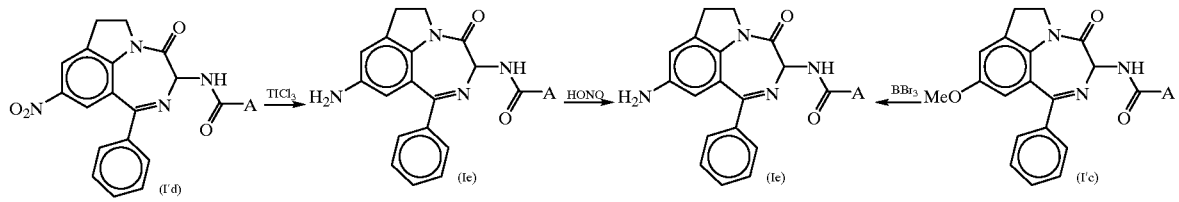

Another aspect of the invention is directed towards a process for the preparation of diazepinoindoles (I), which consists, as shown in Scheme 1:

a) in order to obtain the compounds (Ib) of formula (I) in which B is an —OH group:

in acylating an intermediate aminodiazepinoindole (II$_b$) of formula (II), in which B is an —OH group, with a reactant (III) of formula Z—CO—A, in which A is as defined for (I) and Z represents a halogen, a hydroxyl group, an azido group, an imidazol-1-yl group or a group —O—CO—Z$_1$, it being possible for Z$_1$ to be, besides A, a bulky alkyl or alkoxy radical containing from 3 to 6 carbon atoms, or alternatively Z may be a group O—Z$_2$, Z$_2$ being an aromatic group containing one or two rings substituted with one or more nitro or halo radicals, or in demethylating an intermediate compound (I'$_c$) of formula

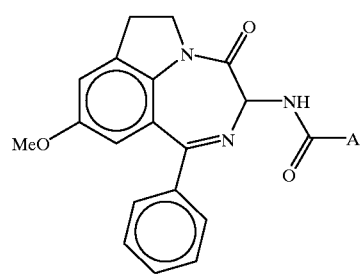

(I'c)

with a boron or aluminum halide, or in diazotizing, in a first step, a compound (I$_e$) of formula (I), in which B is an —NH2 group, and then in hydrolyzing, in a second step, the intermediate diazonium salt, and which consists b) in order to obtain the c ompounds (I$_e$) of formula (I), in which B is an —NH$_2$ group:

in acylating a compound (II$_e$) of formula (II), in which B is an —NH$_2$ group, with the reactant (III) defined above in a), or in reducing the nitro radical of an intermediate compound (I'$_d$) of formula

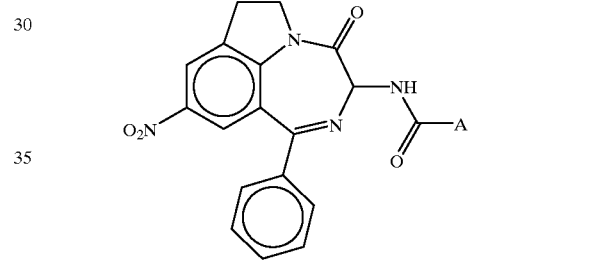

by the action of a metal such as Zn or Sn in acidic medium, or that of a metal chloride or sulfide such as TiCl$_3$ or Na$_2$S, and, as shown in Scheme 2 which follows, which consists:

Scheme 2

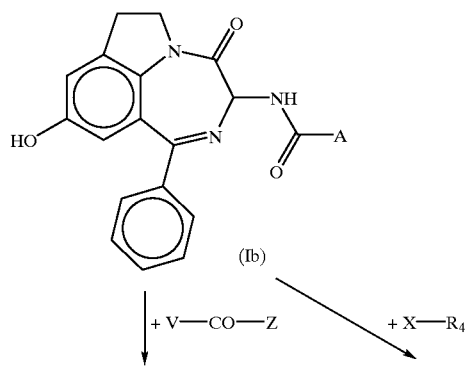

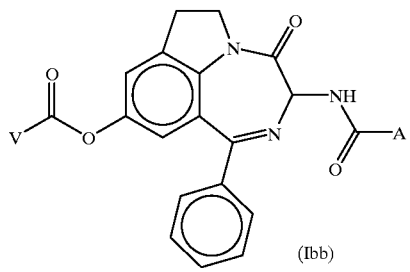

(Ibb)

V= —A, —(CH$_2$)$_{\overline{p}}$—COOH

= —CH═CH—COOH

= -(CH$_2$)$_{\overline{n}}$—CH$_3$

= —(CH$_2$——O·CH$_2$)$_{\overline{p}}$—CH$_2$——O—CH$_3$

= —(CH$_2$——O·CH$_2$)$_{\overline{p}}$—COOH

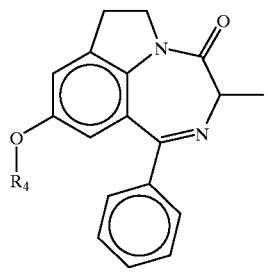

R$_4$ = —CH$_2$—COOH

= —(CH$_2$)$_{\overline{p}}$—N═R$_5$R$_6$

= —(CH$_2$)$_{\overline{p}}$—N<R$_5$R$_6$ c) in order to obtain the compounds (I$_{bb}$) of formula (I), in which B is a group —O—CO—V; V being a group chosen from:
  i) —A, as defined above in a),
  ii) —(CH$_2$)$_p$—CO$_2$H, where p is an integer equal to 2, 3 or 4,
  iii) —CH═CH—CO$_2$H,
  iv) —(CH$_2$)$_n$—CH$_3$, where n is an integer equal to or greater than 0 and less than or equal to 18,
  v) —(CH$_2$—O—CH$_2$)$_p$—CH$_2$—O—CH$_3$, where p is an integer equal to 2, 3 or 4, or
  vi) —(CH$_2$—O—CH$_2$)$_p$—CO$_2$H, where p is an integer equal to 2, 3 or 4,
in esterifying a compound (I$_b$) defined in a), with a reactant (III') of formula V—CO—Z, in which Z has the meaning defined above in a), and which consists d) in order to obtain the compounds (I$_{bc}$) of formula (I), in which B is a group —O—R$_4$, R$_4$ being chosen from:
  i) —CH$_2$—CO$_2$H,
  ii) —(CH$_2$)$_p$—NR$_5$R$_6$, where R$_5$ and R$_6$ are independently —H or lower alkyl, or
  iii) —(CH$_2$)$_p$—N—R$_5$—R$_6$, where R, and R$_6$ form, together with the nitrogen atom to which they are attached, a heterocycle,
in reacting a compound (Ib), defined in a), with a strong base such as an alkali metal hydride, in order to form a phenate, which is reacted with a halide XR$_4$; and, as shown in Scheme 3 which follows, this preparation process also consists:

e) in order to obtain the compounds (I$_{ea}$) of formula (I), in which B is an —NH—C(NH) —NH$_2$ group, in reacting a compound (I$_e$), defined in b), with a guanylating agent such as cyanamide, and f) in order to obtain the compounds (I$_{eb}$) of formula (I), in which B is a group —NH—CO—V, V having the meaning defined in c), in amidating a compound (I$_e$), defined in b), with a reactant (III'): V—CO—Z defined in c), and g) in order to obtain the compounds (I$_{ec}$) of formula (I), in which B is a group —NH—R$_2$, R being lower alkyl or a group R$_4$ as defined in d), in reacting a compound (I$_e$), defined in b), in the presence of a strong base with an alkyl halide XR$_2$, and h) in order to obtain the compounds (I$_{ed}$) of formula (I), in which B is a group —NR$_2$R$_3$, R$_2$ and R$_3$ being lower alkyls, in performing the reductive alkylation of a compound (I$_{ec}$), defined in g), with an aldehyde R'$_3$CHO, in which R'$_3$ is the immediately lower homolog of R$_3$, and, lastly i) in order to obtain the compounds (I$_{ee}$) of formula (I), in which B is a group —N—R$_2$—R$_3$, R$_2$ and R$_3$ forming a heterocycle,
in carrying out a cyclization by reaction of a compound (I$_e$), defined in b), with a reactant of formula X—(CH$_2$)$_l$—Q—(CH$_2$)$_m$—X' in which X and X', which may be the same or different, are halogens, Q is:
  a single valency bond, and 1 and m are integers ranging from 1 to 3 with l+m greater than or equal to 4 and less than or equal to 6,
  an oxygen, a sulfur or a group —NH—, in which case 1 and m are integers ranging from 1 to 3 with l+m greater than or equal to 3 and less than or equal to 5, or, alternately, in alkylating an intermediate diazepinoindole (II$_f$) of formula II wherein B is a group —N—R$_2$—R$_3$, R$_2$ and R$_3$ forming with the nitrogen atom a heterocycle, with a reactant (III) of formula Z—CO—A as previously defined.

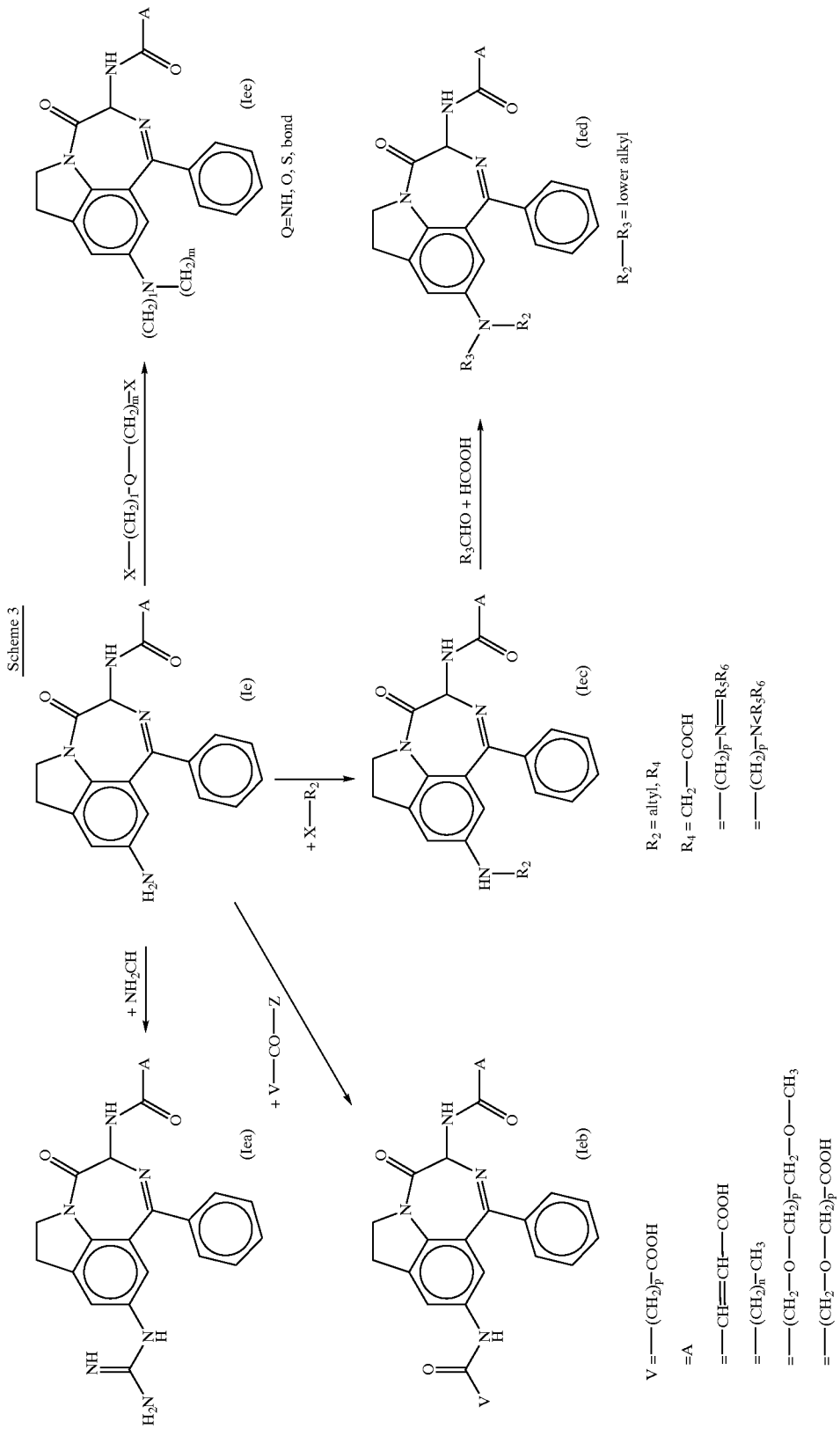

More precisely, the preparation of diazepinoindoles of formula (I) uses, in particular, acylation reactions, in particular in order to obtain the compounds ($I_b$) and ($I_e$) directly from the intermediate amines ($II_b$) and ($II_e$) (Scheme 1). Three processes, referred to as A, B and C, are preferred in order to carry out this step. They are distinguished in particular by the nature of the acylating agent (III), of formula Z—CO—A, employed. Thus, Z represents, depending on the case:

a halogen X when, in the process "A", an acylating agent ($III_A$) of formula X—CO—A is employed;

a pentafluorophenyloxy group when, in the process "B", an acylating agent ($III_B$) of formula $C_6F_5$—O—CO—A is employed;

a hydroxyl radical when, in the process "C", an acylating agent ($III_C$) of formula A—COOH is employed.

According to these three processes, the acylation reaction is performed in an anhydrous organic solvent such as, for example, a chlorinated hydrocarbon such as dichloromethane or chloroform, a linear or cyclic oxide ether such as 1,2-dimethoxyethane, tetrahydrofuran or dioxane, a polar aprotic solvent such as pyridine, dimethyl sulfoxide or dimethylformamide or any other suitable solvent, or alternatively a mixture of several of these solvents.

Advantageously, the reaction is favorably displaced by addition of a base and/or a coupling agent such as an N,N'-disubstituted carbodiimide, N,N'-carbonyldiimidazole or, preferably, O-[(ethoxycarbonyl) cyanomethylamino]-N,N,N',N'-tetramethyluronium tetrafluoroborate or alternatively bromo-tris-pyrrolidinophosphonium hexafluorophosphate.

The operating conditions of processes A, B and C are detailed at the start of the experimental chemical section.

Scheme 1 presents two alternative routes of access to the compounds ($I_b$):

one consists in O-demethylating, with a boron or aluminum halide, an intermediate compound ($I'_c$) whose phenol function was protected by a methyl group; the preferred Lewis acid for this reaction is boron tribromide, in which case the process is performed at an initial temperature of between −70 and −20° C.;

the other consists in diazotizing a compound ($I_e$) with nitrous acid in the presence of inorganic acid and then, in a second step, in hydrolyzing, by heating, the diazonium salt obtained, preferably in the presence of a copper salt.

Scheme 1 indicates that the compound ($I_e$) can also be obtained by reduction of the nitro group of an intermediate compound ($I'_d$), in particular with $TiCl_3$ or $Na_sS$.

Scheme 2 shows the esterification process leading to the diazepinoindoles of formula ($I_{bb}$), which consists in reacting a product of formula ($I_b$) with a carboxylic acid derivative of formula V—(CO)—Z, in which Z has the meaning indicated above and V has the meaning indicated in Scheme 2.

An etherification process, represented in Scheme 2 and leading to the diazepinoindoles of formula ($I_{bc}$), consists in reacting a product of formula ($I_b$) with a strong base such as sodium hydride in order to form a phenate, which is reacted with an alkyl halide $XR_4$, in which $R_4$ is an alkyl radical substituted with a carboxylic acid function, in particular the —$CH_2$—$CO_2H$ radical in a protected form, or alternatively $R_4$ is an alkyl radical substituted with a terminal amine function, in particular the radical —$(CH_2)_p$—$NR_5R_6$, $R_5$ and $R_6$ independently being —H or lower alkyl, or $R_5$ and $R_6$ forming, together with the nitrogen atom to which they are attached, a saturated five- to seven-membered heterocycle which may comprise, as hetero atom which is not directly attached to the nitrogen atom, an oxygen, a sulfur or a nitrogen; and p being an integer equal to 2, 3 or 4. When $R_4$ bears a carboxylic acid function, this function is protected: tert-butyl α-bromoacetate is used, for example; after reaction with the phenate, the product obtained is deprotected with trifluoroacetic acid in order to give the product ($I_{bc}$) where $R_4$=—$CH_2$—$CO_2H$.

Scheme 3 presents:

a process for the preparation of diazepinoindoles of formula ($I_{ea}$), which consists in reacting a diazepinoindole of formula ($I_e$) with cyanamide in acetonitrile; alternatively, N-amidinopyrazole or its 3,5-dimethyl derivative may be used as guanylating agent;

a process for the preparation of diazepinoindoles of formula ($I_{eb}$), which consists in reacting a diazepinoindole ($I_e$) with a carboxylic acid derivative of formula V—(CO)—Z in which Z has the meaning indicated above and V has the meaning indicated in Scheme 3, according to one of the processes A, B and C described above and, preferably, process C;

a process for the preparation of diazepinoindoles of formula ($I_{ec}$), which consists in reacting a product of formula ($I_e$) in the presence of a strong base such as sodium hydride in order to form an amide, which is reacted with an alkyl halide $XR_2$, in which $R_2$ has the meaning indicated in Scheme 3. When $R_2$=$R_4$=—$(CH_2)_p$—$NR_5R_6$, $XR_4$ is used in the form of the hydrochloride;

a process for the preparation of diazepinoindoles of formula ($I_{ed}$), which consists in performing the reductive alkylation of a diazepinoindole ($I_{ec}$), which is reacted with an aldehyde $R'_3CHO$ in which $R'_3$ is the immediately lower homolog of $R_3$, in the presence of formic or acetic acid and a hydride, preferably $NaBH_4$ or $NaBH_3CN$; when ($I_e$) is employed in this reaction, a product ($I_{ed}$) in which B=—$NR_2R_3$, with $R_2$=$R_3$, is obtained directly;

a process for the preparation of diazepinoindoles of formula ($I_{ee}$), which consists in carrying out a cyclization by reaction of a compound ($I_e$) with a reactant of formula X—$(CH_2)_l$—Q—$(CH_2)_m$—X' [sic] in which X and X', which may be the same or different, are halogens, Q is a single valency bond and l and m are integers from 1 to 3 and the sum of which is in the range from 4 to 6; or alternatively Q is —O—, —S— or —NH—, in which case the sum l+m is in the range from 3 to 5. The preferred halogen is bromine.

Intermediates of Formula ($I'_c$) and ($I'_d$)

The processes A, B or, preferably, C, already described, make it possible, as indicated in Scheme 1, to obtain the intermediates ($I'_c$) or ($I'_d$) from the intermediates, ($II_c$) or ($II_d$) of formula (II), in which B represents an —$OCH_3$ or —$NO_2$ group respectively.

The general process for the preparation of the intermediate amines (II) is illustrated in Scheme 4 which follows and is detailed below.

Intermediates of Formula ($II_c$) and ($II_d$)

The amine ($II_c$) may be prepared by nitrating position 9 of a diazepinoindole ($II_a$) with potassium nitrate in sulfuric medium. ($II_d$) in which the —$NO_2$ function may be reduced to —$NH_2$ by a number of reducing agents, including $SnCl_2$, is preferably obtained.

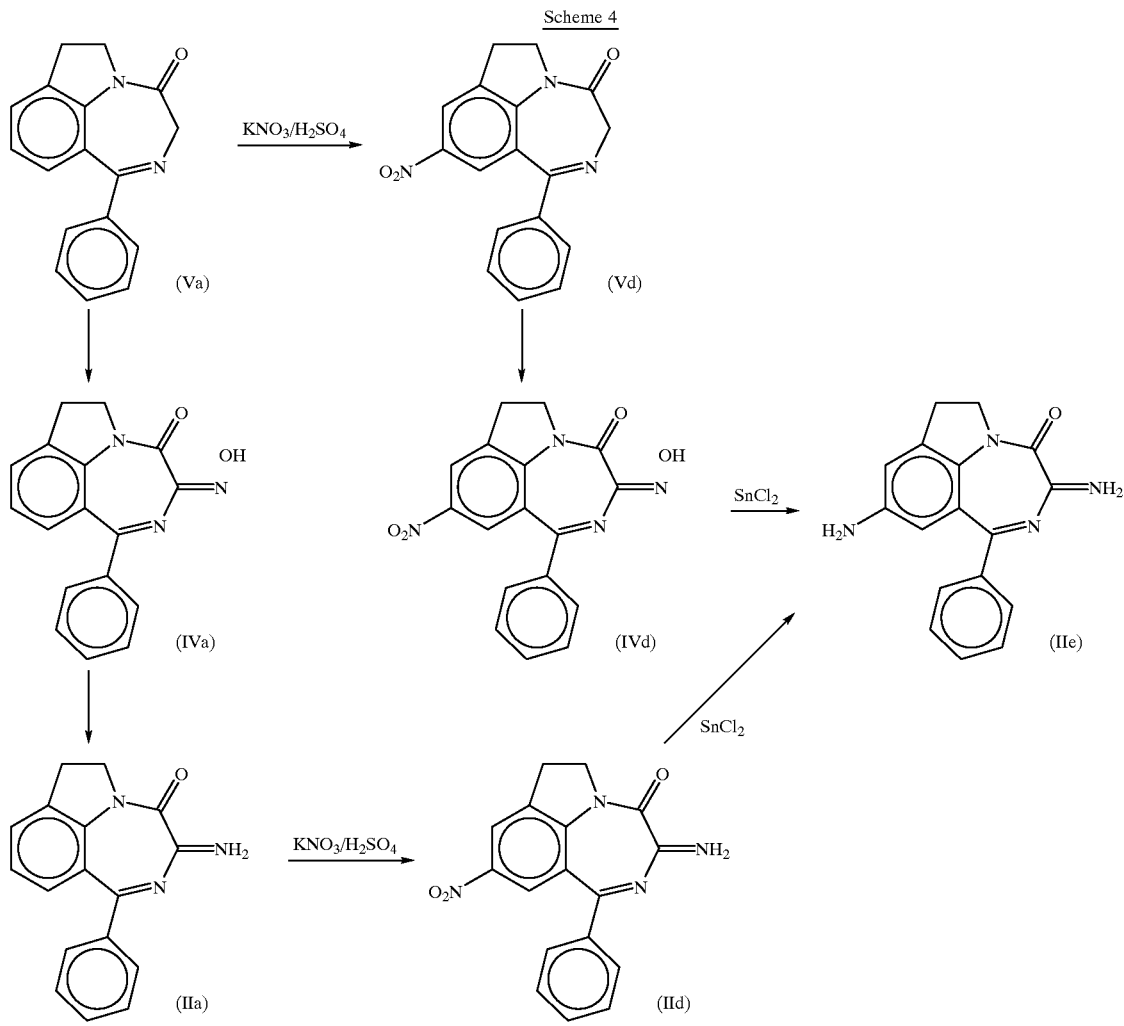

Scheme 4

A variant for the preparation of the intermediate (II$_e$) consists in nitrating a diazepinoindole of formula (V$_a$). An oximating reagent is then reacted with the compound (V$_d$) obtained, in order to obtain the oxime (IV$_d$). Reduction of (IV$_d$) with hydrogen in the presence of a reduction catalyst or by reaction with zinc in the presence of an acid makes it possible to reduce the oxime and nitro functions in order to give (II$_e$).

Intermediate of Formula (II$_f$)

The intermediates are prepared as depicted in Scheme 4 bis by carrying out successively:

i) the protection of the amine function of a nitrated intermediate (II$_d$) in order to obtain an intermediate (II$_{dp}$) including for example a t-butyloxycarbonyl (t.Boc) group, then ii) reducing the nitro group of this intermediate by hydrogenation that can be catalysed for example by ruthenium, to obtain an intermediate (II$_{ep}$), then iii) alkylating the amine function obtained with a reactant of formula X—(CH$_2$)$_1$—Q—(CH$_2$)$_m$—X' previously defined to obtain by cyclization an heterocyclic amine (II$_{fp}$), then iv) to eliminate the protecting group introduced during step i), by reaction with trifluoroacetic acid in anhydrous conditions for the example of a t.Boc protection, yielding to the intermediate (II$_f$).

Scheme 4 bis

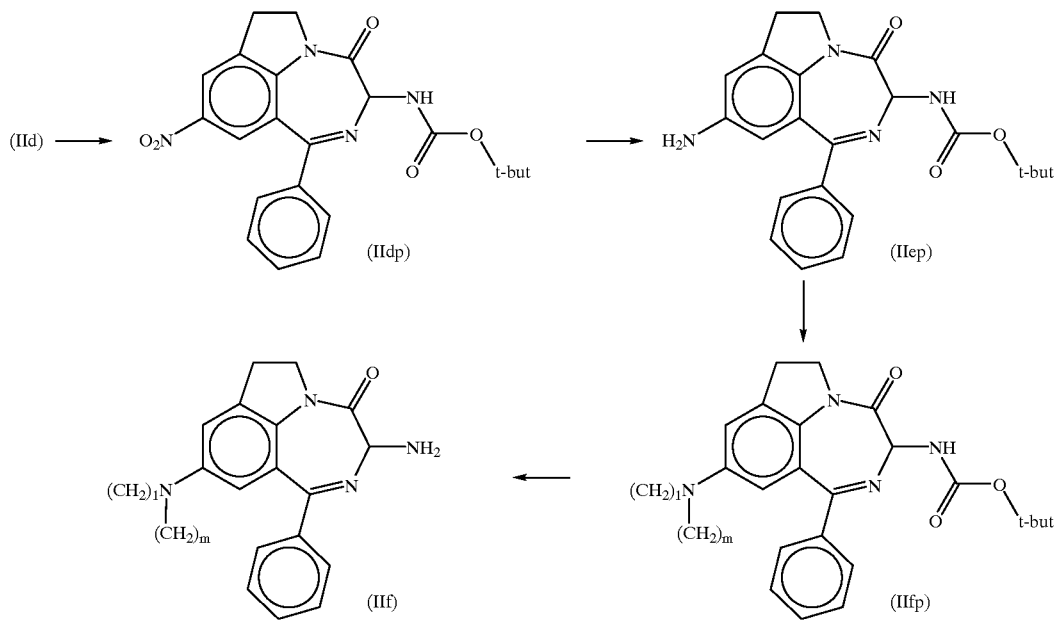

Intermediate of Formula (II$_a$)

The general process for the preparation of the intermediate amines (II$_a$) in their racemic and/or enantiomeric forms is documented in the prior art. For example, an amine of formula (II$_a$) may be prepared by aminating, in a position alpha to the carbonyl, a diazepinoindole of formula (V$_a$) with a hydroxylamine derivative or with chloramine; or alternatively, in two steps, by reacting a compound of formula (V$_a$) with an oximating reagent in order to obtain the oxime of formula (IV$_a$), the second step consisting in catalytically reducing the oxime with hydrogen in the presence of a reduction catalyst or by reaction with zinc in the presence of acetic acid or with stannous chloride in the presence of hydrochloric acid, in order to obtain the amino derivative (II$_a$).

Intermediates of Formula (II$_b$) and (II$_c$)—Scheme 5

The compound (II$_c$) is prepared in two steps, with an oxime intermediate (IV$_c$) and according to a process which is essentially identical to that used to prepare (II$_a$), from a diazepinoindole of formula (V$_c$). (II$_c$) is demethylated to the intermediate (II$_b$) by the action of boron tribromide.

Scheme 6 which follows illustrates the process for the synthesis of (V$_c$):

The indole (IX) is reduced to the corresponding indoline (VIII), which is condensed with benzonitrile (VII) in the presence of Lewis acid in order to give, after hydrolysis, the benzophenone (VI).

The preparation, from (VI) in the presence of ethyl glycinate in pyridine, of the product of formula (V$_c$) is adapted from the method (method N) described by Hester J. B. et al., 1970, J. Med. Chem. 13: 827–835.

In order to prepare an optically active compound of formula (II), among other possibilities, it is possible:

Scheme 5

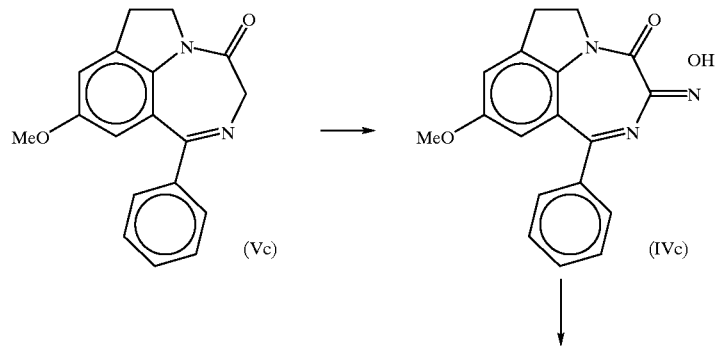

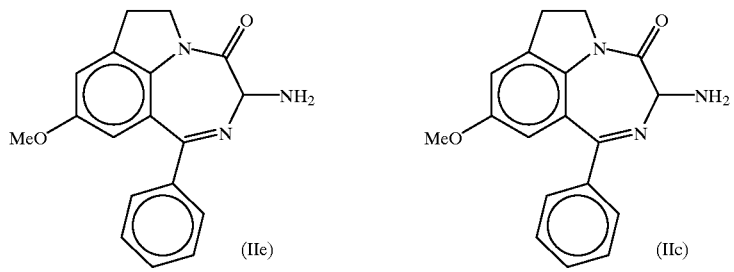

(IIe)  (IIc)

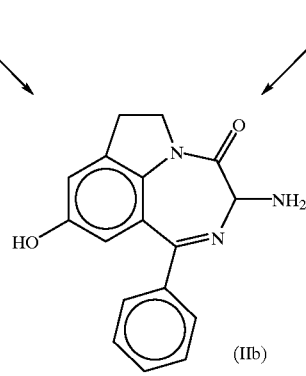

(IIb)

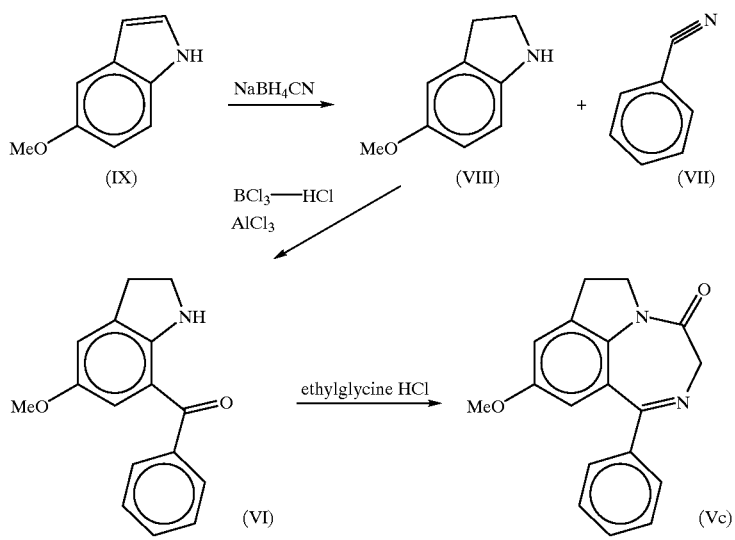

to condense a racemic compound (II) with an alpha-amino acid derivative belonging to the D series or to the L series and in which the amine function is protected with an easily removed group, preferably the tert-butyloxycarbonyl group.

The compound obtained is deprotected by hydrolysis, preferably in acidic medium in the presence of trifluoroacetic acid, and the product obtained is separated into its diastereoisomers by chromatography; the two isomers of the amine condensed with the amino acid are obtained. By Edman degradation, the two enantiomers of the amine (II) are then regenerated; or alternatively, to dissolve a racemic compound (II) in a solution of optically active acid such as, for example, a mandelic, dibenzoyltartaric, di-p-toluyltartaric, camphorsulfonic, p-nitrobenzoylglutamic or tartaric acid enantiomer, in order to form two diastereoisomeric salts, and then using the difference in solubility, to crystallize one of them selectively from a suitable solvent.

The intermediate products of formula (IV) and the products of formula (II) are useful intermediates for the preparation of the active products according to the invention.

The invention is also directed towards a medicinal product for combating inflammatory or allergic diseases, for combating bronchoconstriction, or a medicinal product which is useful in the treatment of asthma, characterized in that it comprises a diazepinoindole according to the invention, in a form which is pharmaceutically adapted to the complaint to be treated.

EXPERIMENTAL SECTION

CHEMICAL SECTION

The following examples illustrate, without, however, limiting it, the use of the processes and products of the invention. The purity, identity and physicochemical characteristics of the essential intermediates and products prepared are determined, thus:

the purity is verified by thin layer chromatography on silica gel (Merck 60-F254) and the Rf observed is reported for the elution solvent used, which is usually identical to that used for the preparative chromatographic purification of the compounds. These solvents are identified by the following abbreviations:

S.A: dichloromethane,
S.A1: dichloromethane - acetone, 97 - 3 (v/v),
S.A2: dichloromethane - acetone, 96 - 4 (v/v),
S.A3: dichloromethane - acetone, 95 - 5 (v/v),
S.A4: dichloromethane - acetone, 90 - 10 (v/v),
S.A5: dichloromethane - acetone, 88 - 12 (v/v),
S.A6: dichloromethane - acetone, 85 - 15 (v/v),
S.A7: dichloromethane - ethyl acet ate, 98 - 2 (V/v),
S.A8: dichloromethane - methanol, 98 - 2 (v/v),
S.A9: dichloromethane - methanol, 97 - 3 (v/v),
S.A10: dichloromethane - methanol, 95 - 5 (v/v),
S.B: ethyl acetate
S.B1: ethyl acetate - cyclohexane, 70 - 30 (v/v),
S.B2: ethyl acetate - cyclohexane, 60 - 40 (v/v),
S.B3: ethyl acetate - methanol, 97 - 3 (v/v),
S.B4: ethyl acetate - methanol, 95 - 5 (v/v),
S.C: methanol, the agreement of the elemental formula of the compounds obtained with that of the target structures is verified by analysis of the main elements. The results are not reported but are indicated in accordance with the structure proposed, taking into account possible solvates or hydrates.

the agreement of the products obtained with the structures proposed is verified by their proton nuclear magnetic resonance spectrum and by their infrared spectrography.

The $^1$H NMR spectra are performed at 400 MHz on a Brüker machine, the compounds being dissolved in deuterochloroform with tetramethylsilane as internal reference. The nature of the signals, their chemical shifts in ppm, the number of protons which they represent and their capacity for exchange with $D_2O$ are recorded.

The infrared spectra are recorded as potassium bromide pellets on a Shimadzu IR-435 spectrometer.

the physicochemical characteristics noted are their melting point, determined by the capillary tube method and whose reported values are uncorrected, and their optical rotation, determined at room temperature in the region of 20° C., on a Polartronic machine in a cell 10 cm in length, and whose results make it possible in certain cases to evaluate the optical purity by calculating the enantiomeric excess (e.e.).

For the purposes of standardization, the chemical nomenclature of the products in the examples is that determined using the "Autoname" program version 1.0 (Beilstein Institute—Ed. Springler) which generates the systematic nomenclatures of the compounds according to the IUPAC rules.

As described above, the preparation of the compounds (I) of the invention uses the reaction of the intermediate amines (II) with halides ($III_A$) according to process A, of the esters, in particular pentafluorophenyl esters ($III_B$), according to process B, or of the carboxylic acids ($III_C$) according to process C. The general procedures of these processes are the following.

Process A: 10.0 mmol of an intermediate amine (II) are dissolved in 60 ml of anhydrous dichloromethane with stirring, in a reactor protected from moisture. 10.0 mmol of acid halide ($III_A$) are then added, followed by dropwise addition of 10.0 mmol of triethylamine, at a temperature in the region of 20° C. The reaction is continued with stirring at a room temperature of between 15 and 25° C. and its progress is monitored by thin layer chromatography. When the reaction is considered to be complete, 120 ml of dichloromethane are added to the reaction medium, the mixture is extracted successively with 60 ml of 1N HCl solution, 60 ml of saturated sodium bicarbonate solution and, finally, 60 ml of water. After drying, the dichloromethane is evaporated off under reduced pressure and the residue is purified by flash chromatography on a column of silica, according to a method adapted from Still et al. (1978) J. org. Chem. 43: 2923, the elution solvent being a mixture of increasing polarity consisting, for example, of acetone in dichloromethane. The elution fractions determined to contain the pure compound are combined and then evaporated under reduced pressure. The residual purified product is subjected to the structure and purity determinations described above.

Process B:

Stage 1: 10.0 mmol of an intermediate acid ($III_c$) of formula A—COOH and 3.55 g (19.3 mmol) of pentafluorophenol are dissolved in 25 ml of dichloromethane. 0.81 g (2.6 mmol) of para-dimethylaminopyridinium para-toluenesulfonate and:

either 22.4 mmol of dicyclohexylcarbodiimide in process "B.a", or 22.4 mmol of N-(3-dimethylaminopropyl)-N'-ethylcarbodiimide in process "B.b", are then added.

The mixture is stirred for 16 hours at the temperature of the laboratory, in the region of 20° C., and the insoluble material is then filtered off. The solvent is eliminated by distillation and the residue is purified by the technique of flash chromatography on a column of silica, usually using a gradient of acetone in dichloromethane as the elution solvent. The fractions determined to be pure by TLC are combined, the solvent is evaporated off and, after analysis, the residual intermediate ester ($III_B$), in the form of an amorphous foam, is used without further purification in the following stage.

Stage 2: 10.0 mmol of the pentafluorophenyl ester ($III_B$) prepared in the above stage are added to 10.0 mmol of intermediate amine (II) dissolved in anhydrous ethyl acetate. After stirring for 16 hours at a room temperature in the region of 20° C., the insoluble material is filtered off, the ethyl acetate is evaporated off under vacuum and the residue is then purified by the technique of flash chromatography on a column of silica, usually using a gradient of methanol in dichloromethane as elution solvent. The fractions determined to be pure by TLC are combined, the solvent is evaporated off and the purified residue is identified and analyzed.

Process C (preferred): 10.0 mmol of an intermediate amine (II) are dissolved in 50.0 ml of anhydrous dichloromethane with stirring, in a reactor protected from moisture. At the temperature of the laboratory, in the region of 20° C., 11.0 mmol of an intermediate acid ($III_c$) of formula A—COOH are then added, followed by 10.0 mmol (3.28 g) of "TOTU"

(abbreviated name for O-[(ethoxycarbonyl) cyanomethylamino]-N,N,N',N'-tetramethyluronium tetrafluoroborate—supplier Fluka, ref. 02580). The mixture is cooled to 0° C., 20.0 mmol (2.55 g) of N,N-diisopropylethylamine are then added, after which the mixture is stirred for 12 hours at room temperature and then extracted successively with 50 ml of 1N HCl solution, 50 ml of saturated sodium bicarbonate solution and, lastly, 50 ml of water.

The solvent is evaporated off under vacuum and the residue is purified by the technique of flash chromatography on a column of silica, usually using a gradient of methanol in dichloromethane as elution solvent. The fractions determined to be pure by TLC are combined, the solvent is evaporated off and the purified residue is identified and analyzed.

Intermediate Compounds (II)

Intermediate 1: (3R)-3-Amino-1-phenyl-6,7-dihydro-3H-[,1,4]diazepino[6,7,1-hi]indol-4-one[(IIa)-R; B=H]

The preparation of the compound in its racemic form is described in Example 1 stages a) and b) of EP 0,340,064 A1. Similarly, that of the (R) enantiomer is described in Example 5 stages a) b) c) g) and h) of the same application. However, an alternative method which consists in resolving the racemic compound by the formation and separation of diastereoisomers with N-acetyl-L-phenylalanine is preferred, and this method is reported below:

74.0 g (267 mmol) of (3R,S)-3-amino-1-phenyl-6,7-dihydro-3H-[1,4]diazepino[6,7,1-hi]indol-4-one are dissolved in 210 ml of boiling n-propanol. Meanwhile, 44.1 g (267 mmol) of N-acetyl-L-phenylalanine are dissolved in 140 ml of boiling n-propanol. The two solutions are mixed together, left to cool and then seeded with a few crystals. After leaving to stand for three days, the crystals are filtered off and dried. Weight: 50.0 g (e.e. =77%).

The product is recrystallized twice successively from boiling ethyl acetate. 39.0 g (e.e.=97%) are obtained. The mother liquors of the first crystallization are evaporated and the residue is taken up in boiling ethyl acetate. After crystallization, filtration and drying, 35.0 g of crystals (e.e= 50%) are obtained, which, after two successive crystallizations from boiling ethyl acetate, allow 17.0 g (e.e.=97%) of product to be obtained. The two combined crops represent 56.0 g (yield=95%) of the salt of the 3R enantiomer of the amine with N-acetyl-L-phenylalanine. m.p.=171° C. $[\alpha]_D$=+132° (c=1, methanol).

42.4 g (96 mmol) of the salt of the (3R) amine are stirred vigorously in the presence of 500 ml of ethyl acetate and 500 ml of normal sodium hydroxide. After dissolution, the ethyl acetate phase is separated out, washed with water saturated with sodium chloride and then dehydrated and evaporated. 25.4 g of the expected amine are obtained.

Yield=95%. m.p.=79° C. $[\alpha]_D$=172° (c=1, $CH_2Cl_2$). $^1$H NMR δ (ppm): 3.05–3.5 (m, 2H); 3.3 (broad s, 2H exch.); 3.9–4.0 (m, 1H); 4.6–4.7 (m, 1H); 7.05–7.6 (m, 9H). I.R.: 3350, 1670, 1600, 1560, 1420, 1380, 1340, 1290, 1240, 760, 730, 690 cm$^{-1}$.

Intermediate 2: (3R)-3,9-Diamino-1-phenyl-6,7-dihydro-3H-[1,4]diazepino[6,7,1-hi]indol-4-one [(IIe)-R; B=—$NR_2R_3$; $R_2$=$R_3$=H].

Stage 1: 51.0 ml of concentrated sulfuric acid (d=1.83) are introduced into a 100 ml reactor and, with stirring, 16.0 g (57.7 mmol) of (3R)-3-amino-1-phenyl-6,7-dihyro-3H-[1,4] diazepino[6,7,1-hi]indol-4-one, intermediate 1 described above, are added. During the exothermic introduction, the temperature reaches 70° C.; the brown solution obtained is cooled to 5–10° C. 6.93 g (68.5 mmol) of pure potassium nitrate dissolved in 17.0 ml of sulfuric acid (d=1.83) are then introduced rapidly. The temperature rises to 40° C. and is then maintained at 20° C. with stirring for 40 minutes. The brown solution is precipitated in 600 ml of a mixture of ice and water. The mixture is basified with concentrated aqueous ammonia solution and then extracted with 3 times 150 ml of dichloromethane. The organic phases are washed with water and dehydrated, and the solvents are then eliminated by distillation. A light-brown foamy residue (17.5 g) is obtained, which is purified by flash chromatography on silica. Elution with dichloromethane progressively enriched with methanol allows 12.0 g of purified (3R)-3-amino-9-nitro-1-phenyl-6,7-dihydro-3H-[1,4]-diazepino[6,7,1-hi] indol-4-one [(IId)- R; B=$NO_2$] to be obtained. Yield=75% m.p.=177–178° C. $[\alpha]_D$=+66.8° C. (c=0.4, $CH_2Cl_2$)

Stage 2: 13.0 g (40.3 mmol) of the nitro derivative obtained in the above stage, 45.5 g (202 mmol) of tin chloride dihydrate and 81 ml of ethanol are introduced into a 250 ml reactor. The mixture is brought to 70° C. with stirring and is maintained at this temperature for 30 minutes. A brown solution is obtained, and about 60 ml of solvent are then distilled off. The residue is taken up in 400 ml of ice-water and the aqueous phase and the insoluble gum are extracted with ether.

The ether phase is discarded. The aqueous phase and the gum are basified with sodium hydroxide solution to pH 12. The mixture is extracted with 3 times 150 ml of dichloromethane. The combined organic phases are washed and dried and the dichloromethane is then eliminated by distillation. The residue (13.0 g) is purified by chromatography on a column of silica, eluting with dichloromethane progressively enriched with methanol. 12.4 g of (3R) -3,9-diamino-1-phenyl-6,7-dihydro-3H-[1,4]diazepino[6,7,1-hi]indol-4-one [intermediate (II$_e$)—R; B=—$NR_2R_3$; $R_2$=$R_3$=H] are obtained.

$^1$H NMR δ (ppm): 7.5–7.65 (m, 2H); 7.5–7.3 (m, 3H); 6.8 (d, 1H); 6.4 (d, 1H); 4.5–4.65 (m, 1H); 3.8–4 (q, 1H); 3.15–3.3 (m, 1H); 2.95–3.05 (m, 1H); 2.50–4.00 (m, 2H) I.R.: 3300, 3200; 1660, 1580, 1480, 1440, 1360, 1240, 710 cm$^{-1}$.

Intermediates 3

3.a: (3R,S)-3-Amino-9-methoxy-1-phenyl-6,7-dihydro-3H-[1,4]diazepino[6,7,1-hi]indol-4-one, [(II$_c$) - R,S; B=$CH_3O$]

The compound is prepared from 5-methoxyindole, in 5 stages.

Stage 1: 5-Methoxyindoline.

To a solution of 50.0 g (340 mmol) of 5-methoxyindole in 700 ml of glacial acetic acid are added portionwise, at 15–20° C., 53.4 g (850 mmol) of sodium cyanoborohydride. The weakly exothermic addition is carried out over 3 hours and is accompanied by a slight evolution of hydrogen. The mixture is left stirring below 20° C. for 12 hours, 700 ml of water are then added and the pH of the reaction medium is adjusted to between 10 and 12 by addition of 1200 ml of 30% sodium hydroxide solution. The mixture is extracted twice with dichloromethane and the organic phase is then washed with 300 ml of water. The mixture is evaporated and the residue is purified by flash chromatography on a column of silica, the eluent used being a mixture of increasing polarity of methanol in dichloromethane. 41.84 g of colorless oil which becomes pale yellow on storage (to be stored under nitrogen atmosphere and sheltered from the light) are obtained.

Yield=83%—TLC: S.B2; 0.38. $^1$H NMR δ (ppm): 3.00 (t, 2H); 3.40 (s, 1H exch.); 3.50 (t, 2H); 3.70 (s, 3H); 6.60 (s, 2H); 6.80 (s, 1H).

Stage 2: 7-Benzoyl-5-Methoxyindoline.

5.00 g (33.5 mmol) of 5-methoxyindoline are dissolved in 50 ml of 1,2-dichloroethane. 33.5 ml (33.5 mmol) of boron trichloride as a molar solution in dichloromethane and 6.90 g (67 mmol) of benzonitrile are added dropwise at temp.<5° C. The mixture is heated for 6 hours at reflux (bulk temp.= 82–84° C.). After cooling, hydrolysis is performed by addition of 33.5 ml of 4N hydrochloric acid and heating for 20 minutes at 80° C. The mixture is left: to cool to about 20° C. and is extracted with dichloromethane. The aqueous phase is reextracted with 100 ml of dichloromethane. The combined organic phases are washed with sodium hydroxide solution, then with concentrated sodium chloride solution and are dried over sodium sulfate. After filtration and evaporation, 3.12 g of an orange-yellow solid are obtained.

Yield=38%—m.p.=123° C.—TLC: S.A7; 0.81 $^1$H NMR δ (ppm): 3.05 (t, 2H); 3.65 (s, 3H); 3.75 (t, 2H); 6.75 (broad s, 2H of which 1H exch.); 6.95 (broad s, 1H); 7.40–7.55 (m, 3H); 7.65 (m, 2H).

Stage 3: 9-Methoxy-1-phenyl-6,7-dihydro-3H-[1,4] diazepino[6,7,1-hi]indol-4-one.

4.71 g (18.6 mmol) of 7-benzoyl-5-methoxyindoline are introduced into 75 ml of pyridine, followed by 16.2 g (116 mmol) of ethyl glycinate hydrochloride. The mixture is heated to 110–115° C. with stirring while distilling off the light fractions which form. After 12 hours, the mixture is cooled and 100 ml of a 2.5% solution of sodium carbonate in water and 100 ml of dichloromethane are added. The aqueous phase is separated out and extracted with 100 ml of dichloromethane. The organic phases are combined and washed with water. The solvent is evaporated off and the residue is then purified by flash chromatography on a column of silica, the eluent used being a gradient of acetone in dichloromethane. 4.15 g of purified product in the form of a brown resin are obtained.

Yield=82%—TLC: S.A6; 0.73. $^1$H NMR δ (ppm): 3.10 (t, 2H); 3.70 (s, 3H); 4.30 (t, 2H); 3.90 (s, 2H) 6.60 (s, 1H); 7.00 (s, 1H); 7.30–7.50 (m, 3H); 7.60 (d, 2H).

Stage 4: 3-Hydroxyimino-9-methoxy-1-phenyl-6,7-dihydro-3H-[1,4]diazepino[6,7,1-hi]indol-4-one.

6.78 g (26 mmol) of the above product are dissolved in a mixture of 26 ml of tetrahydrofuran and 51 ml of toluene. The mixture is cooled and, at a temperature below 0° C., 7.29 g (65 mmol) of potassium tert-butoxide are added. The addition is exothermic and the solution turns black. After stirring for 20 minutes, 3.20 g (27.3 mmol) of isoamyl nitrite are added over approximately 10 minutes. The mixture is kept stirring below 0° C. for 10 minutes, followed by addition of 10.3 ml of glacial acetic acid and 100 ml of water. An insoluble material is filtered off and 50 ml of dichloromethane are added. The phases are allowed to separate by settling and the aqueous phase is washed with 100 ml of dichloromethane. The organic phases are combined and washed with 100 ml of water. After evaporation of the solvent, the residue is purified by chromatography. 4.44 g of an orange-yellow solid are obtained.

Yield=53%—m.p.=205° C.; TLC: S.AS; 0.17. $^1$H NMR δ (ppm): 3.20 (t, 2H); 3.70 (s, 3H); 4.40 (t, 2H); 6.70 (t, 2H); 7.10 (s, 1H); 7.40–7.60 (m, 3H); 7.80 (d, 2H); 8.60 (s, 1H).

Stage5: (3R,S)-3-Amino-9-methoxy-1-phenyl-6,7-dihydro-3H-[1,4]diazepino[6,7,1-hi]indol-4-one.

4.38 g of 5% ruthenium-on-charcoal are added to a solution of 14.6 g (45 mmol) of the product obtained in the above stage in 1.0 l of methanol. The mixture is hydrogenated at a pressure of 8 bar at 80° C. for 6 hours and the catalyst is then filtered off and rinsed. After evaporation, the residue is purified by flash chromatography on a column of silica, the eluent used being a mixture of dichloromethane progressively enriched with methanol. 9.66 g of purified amine are obtained in the form of a beige-yellow solid.

Yield=67%—m.p.=84OC; TLC: S.B3; 0.24. $^1$H NMR δ (ppm): 3.20 (t, 2H); 3.70 (s, 3H); 4.40 (t, 2H); 5.30 (s, 1H); 6.70 (s, 1H); 7.10 (s, 1H); 7.40–7.80 (m, 5H); 8.10 and 8.50 (broad s, 2H exch.).

3.b: (3R)-3-Amino-9-methoxy-1-phenyl-6,7-dihydro-3H-[1,4]diazepino[6,7,1-hi]indol-4-one [(II$_c$)-R; B=CH$_3$O]

10.0 g (32.3 mmol) of the (R,S) amine, intermediate 3.a., are dissolved in 100 ml of refluxing acetonitrile. Meanwhile, 12.47 g (32.3 mmol) of di-paratoluoyltartaric acid are dissolved at reflux in 100 ml of acetonitrile. The hot solutions are mixed together and then left to crystallize by cooling to the temperature of the laboratory. After leaving to stand overnight, the white crystals are filtered off, washed with 100 ml of cold acetonitrile and then dried. These crystals (e.e.=37%) are recrystallized twice successively from acetonitrile in order to obtain the purified product (e.e.=99.5%). This purification is followed by chromatography on an optically active Pirckle-type $C_{18}$ column, eluting with a 50/50 mixture of isopropanol and n-hexane% 9.9 g of product are obtained. Yield=44%. m.p. =168° C.

The 9.9 g of the above salt are suspended in 100 ml of ethyl acetate. Saturated sodium bicarbonate solution is added with vigorous stirring and, after a few minutes, the aqueous phase is discarded. The organic phase is washed with 50 ml of water and dried, and the solvent is then evaporated off while cold under a nitrogen atmosphere. 4.1 g of purified base are obtained.

Yield =95% —m.p.=84° C.—[α]$_D$=+23° (c=1, CH$_2$Cl$_2$).

3.c: (3R)-Isoquinoline-3-carboxylic acid (9-methoxy-4-oxo-1-phenyl-3,4,6,7-tetrahydror[1,4]diazepino [6,7,1-hi]indol-3-yl)amide
[(I'$_c$); A=3-isoquinolyl, B=CH$_3$O]

The compound is prepared as described in the general process B with the above intermediate 3.b and the pentafluorophenyl isoquinoline-3-carboxylate intermediate.

Yield=87%—white solid—m.p.=211° C.—[α]$_D$=+0.30° (c=1, CH$_2$Cl$_2$); TLC: S.B1; 0.30 $^1$H NMR δ (ppm): 3.10 (m, 1H); 3.35 (m, 1H); 3.75 (s, 3H); 4.00 (m, 1H); 4.70 (m, 1H); 5.70 (d, 1H s. by exch.); 6.70 (broad s, 1H); 7.10 (broad s, 1H); 7.20–7.80 (m, 7H); 8.00 (d, 1H); 8.10 (d, 1H); 8.65 (s, 1H); 9.30 (s, 1H); 9.90 (d, 1H exch.) I.R.: 3360, 1665, 1500, 1490, 1470, 1345, 1265, 1225, 1145, 700 cm$^{-1}$.

Intermediate 4

(3R)-3-amino-1-phenyl-9-(pyrrolidin-1-yl) 6,7-dihydro-3H-[1,4]diazepino[6,7,1-hi]indol-4-one, [(II$_f$)-R; B=—NR$_2$R$_3$; —R$_2$—R$_3$—=—(CH$_2$)$_4$—]

Stage 1 : i) 13.0 g (40.3 mmol) of (3R)3-amino-9-nitro-1-phenyl-6,7-dihydro-3H-[1,4]diazepino[6,7,1-hi]indol-4-one [compound (IId); B=NO$_2$ prepared at intermediate 2—stade 1] in 78 ml of THF dehydrated over molecular sieves are introduced in a reactor protected from moisture and under a nitrogen atmosphere.

The solution is cooled to a t<5° C., under agitation 10.56 g (48.4 mmol) of t-butylcarbonate in 40 ml THF are added. The temperature is allowed to reach 20–25° C. and leave 16 hours still. Solvents are eliminated by distillation on a hot waterbath and under vacuum, the residue is taken up with 100 ml petroleum ether, filtered and dried (Yield: 100%). (3R)-N-(9-nitro-4-oxo-1-phenyl-6,7-dihydro-3H-[1,4] diazepino[6,7,1-hi]indol-3-yl)-t-butyloxycarbamide (IIdp) as obtained is directly reacted in the next step.

ii) 11.0 g (26 mmol) of the intermediate obtained at the latter step in one liter of methanol and 4.0 g of charcoal at 5% ruthenium are introduced into a hydrogenation reactor, which is filled with hydrogen. The reduction is carried out at 85° C. for 6 hours. The catalyst is filtered out, the solvent is eliminated by distillation under vacuum, and the residue is purified by rapid chromatography on a column of silica. Elution by dichloromethane containing 2 % (v/v) methanol followed by elimination of the solvents yields (3R)N-(9-amino-4oxo-1-phenyl-6,7-dihydro-3H-[1,4]diazepino[6,7,1-hi]indol-3-yl)-t-butyloxy-carbamide (IIep) purified, in amorphous state.

Mass: 8.8 g—Yield: 86 %—TLC: S.A8 Rf: 0.40

Stage 2: in 150 ml of anhydrous dimethylformamide (DMF), 6.0 g (15.3 mmol) of intermediate (IIep), 3.60 ml (6.60 g or 30.6 mmol) of 1,4-dibromobutane and 6.38 g (76 mmol) of sodium hydrogen carbonate are introduced into a reactor protected from moisture.

The suspension is heated to 60° C. and agitated for 7 hours, then the DMF is distilled off under vacuum; the residue is taken up in 150 ml dichloromethane. The solution is extracted with water, then dried; the solvent is distilled off under vacuum and the residue is purified by rapid chromatography on a column of silica. Elution by dichloromethane containing 1% (v/v) methanol yields to 4.10 g of (3R)N-4-oxo-1-phenyl-9-(pyrrolidin-1-yl)-6,7-dihydro-3H[1,4] diazepino [6,7,1-hi]indol-3-yl) t-butyloxy-carbamide (IIfp) purified. Yield=60%—TLC: S.A8 Rf: 0.60.

Stage 3: In a reactor protected from moisture, 48 ml of anhydrous dichloromethane and 4.10 g (9.2 mmol) of intermediate (IIfp) obtained in the previous step are introduced. To the solution 24.75 ml (36.34 g or 321 mmol) pure trifluoroacetic acid (d=1.48) are added dropwise at room temperature. The mixture is agitated for 2 hours at 20–25° C. then the solvents are eliminated by distillation under vacuum. The residue is purified by rapid chromatography on a column of silica, elution with dichloromethane containing 5% (v/v) methanol yields, after removal of the solvents, a purified product in an amorphous state. Mass=4.35 g.

The product is salified with trifluoroacetic acid. It is taken up by a satured sodium bicarbonate solution and the mixture is extracted with dichloromethane. After evaporation, (3R)-3-amino-1-phenyl-9-(pyrrolidin-1-yl)6,7-dihydro-3H-[1,4] diazepino[6,7,1-hi]indol-4-one (IIf) is obtained in an amorphous state. Mass 3.00 g; Yield : 71%—TLC: S.A8 Rf: 0.80.

EXAMPLES OF THE INVENTION (I)

Example 1

(3R)-Isoguinoline-3-carboxylic acid (9-hydroxy-4-oxo-1-phenyl-3,4,6,7-tetrahydro-[1,4]diazepino[6,7,1-hi]indol-3-yl)amide

[($I_B$); A=Isoquinolyl; B=—$OR_1$, $R_1$=H]

1.00 g (2.2 mmol) of the intermediate 3.c (3R)-isoquinoline-3-carboxylic acid (9-methoxy-4-oxo-1-phenyl-3,4,6,7-tetrahydro[1,4]diazepino[6,7,1-hi]indol-3-yl)-amide in 20.0 ml of dichloromethane dehydrated over molecular sieves is dissolved in a 50 ml reactor protected from moisture and under a nitrogen atmosphere.

The solution is cooled to −50° C. and 5.41 g (22 mmol) of boron tribromide are added rapidly with stirring.

The brown, heterogeneous mixture is stirred at 20–25° C. for 3 hours and is then precipitated in a mixture of 50 ml of water and 30 ml of dichloromethane. The insoluble material is filtered off, the aqueous phase is discarded and the dichloromethane is evaporated off.

The evaporation residue and the insoluble material are combined and purified by chromatography on a column of silica. Elution with the mixture S.A8 allows 0.48 g of yellow, amorphous purified product to be obtained. Yield= 49.5% —m.p. =215° C.

Analysis in agreement for $C_{27}H_{20}N_4O_3$ —(0.15 $CH_2Cl_2$) —(0.25 $H_2O$)—TLC: S.A1; 0.33 $^1H$ NMR δ (ppm): 3.10 (m, 1H); 3.35 (m, 1H); 3.95 (m, 1H); 4.50 (m, 1H); 5.40 (d, 1H); 6.05 (d, 1H); 7.1 (d, 1H); 7.45 (m, 5H); 7.90 (m, 2H); 8.30 (m, 2H); 8.65 (s, 1H); 9.50 (s, 1H); 9.70 (d, 1H, exch. $D_2O$); 9.75 (s, 1H, exch. $D_2O$). I.R.: 3450, 3200, 1680, 1660, 1620, 1590, 1510, 1460, 1440, 1370, 1320, 1270, 1230, 1140, 1100, 1060, 960, 860, 760, 740, 700, 630, 540, 490 $cm^{-1}$.

Example 2

(3R)-4-t-Butyloxycarbonylamino-N-(9-amino-4-oxo-1-phenyl-3,4,6,7-tetrahydro[1,4]diazepino[6,7,1-hi]indol-3-yl)benzamide

[($I_e$); A=4-t-butyloxycarbonylaminophenyl; B=—$NR_2R_3$; $R_2$=$R_3$=H]

1.60 g (5.5 mmol) of (3R)-3,9-diamino-1-phenyl-6,7-dihydro-3H-[1,4]diazepino[6,7,1-hi]indol-4-one (intermediate 2) are dissolved, with stirring, in 60.0 ml of anhydrous dichloromethane in a reactor protected from moisture. 1.44 g (6.05 mmol) of 4-t-butoxycarbonylamino-benzoic acid are then added at about 20° C., followed by 1.80 g (5.5 mmol) of "TOTU" (abbreviated name for O-[(ethoxycarbonyl)cyanomethylamino]-N,N,N'N'-tetramethyluronium tetrafluoroborate—supplier Fluka, ref. 02580). The mixture is cooled to 0° C. and 1.9 ml, i.e. 1.42 g (11.0 mmol) of N,N-diisopropylethylamine are added, after which the mixture is stirred for 12 hours at room temperature and then extracted successively with 50 ml of 1N HCl solution, 50 ml of saturated sodium bicarbonate solution and, lastly, 50 ml of water. The solvent is evaporated off under vacuum and the residue, weighing 2.75 g, is purified by the technique of flash chromatography on a column of silica, using an 80/20 v/v ethyl acetate/hexane mixture as elution solvent. The fractions determined to be pure by TLC are combined, the solvent is evaporated off and the purified residue (1.78 [lacuna]) is solubilized in 6 ml of isopropanol and then precipitated by addition of 100 ml of hexane. The product is filtered off and dried under vacuum.

Weight: 1.30 g. Yield=46%—yellow powder—m.p.= 215–225° C.—[α]$_D$=+47° (C=1, $CH_2Cl_2$). Analysis in agreement for $C_{29}H_{29}N_5O_4$—TLC: S.B; 0.45 $^1HMR$ δ (ppm): 1.50 (s, 9H); 2.95–3.10 (m, 1H); 3.20–3.35 (m, 1H); 3.80 (s, 2H); 3.85–4.00 (m, 1H); 4.55–4.70 (m, 1H); 5.55–5.65 (d, 1H); 6.40 (d, 1H); 6.85 (d, 1H); 7.15 (s, 1H); 7.30–7.60 (m, 7H); 7.80–7.95 (d, 2H); 7.95– 8.05 (d, 1H). I.R.: 3300, 2995, 1640, 1470, 1370, 1310, 1230, 1150, 1050, 700 $cm^{-1}$.

Example 3

(3R)-4-Amino-N-(9-amino-4-oxo-1-phenyl-3,4,6,7-tetrahydro[1,4]diazepino[6,7,1-hi]indol-3-yl)benzamide

[($I_e$) ; A=4-aminophenyl; B=—$NR_2R_3$; $R_2$=$R_3$=H]

1.00 g (1.95 mmol) of (3R)-4-t-butyloxycarbonyl- amino-N-(9-amino-4-oxo-1-phenyl-3,4,6,7-tetrahydro[1,4]-diazepino[6,7,1,-hi]indol-3-yl)benzamide (product of Example 2) is dissolved with stirring in 30 ml of anhydrous dichloromethane, in a 50 ml reactor.

The pale yellow solution is cooled to 0° C. and 10.0 ml of trifluoroacetic acid (d=1.480) are added, without exceeding 5° C. The reaction medium, which becomes orange-red, is kept stirring at 0–5° C. for 45 minutes. It is then evaporated under vacuum on a water bath.

The residue is taken up in 100 ml of dichloromethane and washed with 2N NaOH solution and then with water. The solvent is then evaporated off under vacuum and 0.85 g of a yellow residue is obtained, which is purified by flash chromatography on a column of silica, eluting with the mixture S.A8. The evaporated purified fractions give 0.60 g of yellow product, which are crystallized at about 20° C. from 20 ml of isopropanol. The insoluble material is filtered off and dried. Weight: 0.50 g.

Yield=60%—yellow powder—m.p.=276° C.—$[\alpha]_D$.=+63° (c=1, MeOH).

Analysis in agreement for $C_{24}H_{21}N_5O_2$-(0.25 i-PrOH)—TLC: S.A3; 0.20. $^1H$ NMR δ (ppm): 2.95–3.10 (m, 1H); 3.15–3.35 (m, 1H); 3.75–3.90 (m, 1H); 4.35–4.50 (m, 1H); 5.30 (s, 2H); 5.40–5.50 (d, 1H); 5.75 (s, 2H); 6.35 (d, 1H); 6.55–6.65 (d, 2H); 6.85 (d, 1H); 7.40–7.60 (m, 5H); 7.70–7.80 (d, 2H); 8.85–8.95 (d, 1H). I.R.: 3300, 1600, 1475, 1370, 1270, 1180, 830, 765, 695, 530 $cm^{-1}$.

Example 4

(3R)-4-Amino-N-(9-amino-4-oxo-1-phenyl- 3,4,6,7-tetrahydro[1,4]diazepino [6,7,1-hi]indol-3-yl)-3,5-dichlorobenzamide

[($I_e$); A=4-amino-3,5-dichlorophenyl; B=—$NR_2R_3$; $R_2$=$R_3$=H]

The compound is prepared according to the procedure of Example 2, starting with the intermediate amine 2 and 4-amino-3,5-dichlorobenzoic acid.

After reaction, the residue is purified by flash chromatography on a column of silica, eluting with the mixture S.A8. The product obtained is finally recrystallized from ethyl acetate.

Yield=55%—yellow powder—m.p.=>280° C.—$[\alpha]_D$=+48.5° (c=1, MeOH). Analysis in agreement for $C_{24}H_{19}Cl_2N_5O_2$ $^1H$ NMR δ (ppm): 2.85–3.05 (m, 1H); 3.20–3.35 (m, 1H); 3.80–3.90 (m, 1H); 4.40–4.50 (m, 1H); 5.20–5.30 (m, 2H); 5.45 (d, 1H); 6.10 (s, 2H); 6.40 (s, 1H); 6.90 (s, 1H); 7.40–7.60 (m, 5H); 8.00 (s, 2H); 9.45 (d, 1H). I.R.: 3300, 3200, 1670, 1610, 1510, 1480, 1380, 1280, 1240, 1180, 1130, 850, 790, 700 $cm^{-1}$.

Example 5

(3R)-4-Amino-N-[9-(4-amino-3,5-dichlorobenzamido)-4-oxo-1-phenyl-3,4,6,7-tetrahydror[1,4]-diazepino[6,71-hi]indol-3-yl]-3,5-dichlorobenzamide

[($I_{eb}$); A=4-amino-3,5-dichlorophenyl; B=—$NR_2R_3$; $R_2$=—CO—A; $R_3$=H]

The impure fractions obtained on the chromatographic treatment of Example 4 above are combined and evaporated under vacuum. The residue is taken up and treated by flash chromatography on a column of silica, eluting with dichloromethane progressively enriched with acetone. The purified product is eluted with the mixture in proportions of 80/20 (v/v). Weight after evaporation: 0.20 g—beige-white powder—m.p.=>220° C.

Analysis for $C_{31}H_{22}N_6O_3Cl_4$—(0.5 $CH_3$—CO—$CH_3$) TLC: S.A3; 0.60 $^1H$ NMR δ (ppm): 3.00–3.15 (m, 1H); 3.15–3.30 (m, 1H); 3.95 (q, 1H); 4.50–4.60 (m, 1H); 4.80 (s, 2H); 4.90 (s, 2H); 5.40 (d, 1H); 7.20–7.45 (m, 6H); 7.70 (s, 2H); 7.80 (s, 2H); 7.85 (d, 1H); 7.95 (s, 1H); 8.70 (s, 1H) I.R.: 3250, 1610, 1530, 1480, 1370, 1260, 880, 780 $cm^{-1}$.

Example 6

(3R)-2-Acetylamino-N-(9-amino-4-oxo-1-phenyl-3,4,6,7-tetrahydro[1,4]diazepino[6,7,1-hi]indol-3-yl) benzamide

[($I_e$) ; A=2-acetylaminophenyl; B=—$NR_2R_3$; $R_2$=$R_3$=H]

1.23 g (6.84 mmol) of 2-acetylaminobenzoic acid are dissolved in 40 ml of anhydrous tetrahydrofuran (THF) [lacuna] 0.76 g (7.5 mmol) of 4-methylmorpholine, in a 100 ml reactor protected from moisture and under a nitrogen atmosphere.

The solution is stirred for 5 minutes and then cooled to −20° C., 0.93 g (6.84 mmol) of isobutyl chloroformate are next added and the white suspension is then kept stirring at −20° C. for 30 minutes. 2.00 g (6.84 mmol) of the intermediate amine 2 dissolved in 11 ml of THF are then added at this same temperature.

The suspension is kept stirring for one hour at −20° C., and then for 2 hours at 0° C. After this, the insoluble material is filtered off, the filtrate is concentrated under vacuum and the residue is purified by flash chromatography on a column of silica. The column is eluted with dichloromethane and 1.5 g of amorphous purified product are recovered, which product is crystallized from 100 ml of ethyl ether. The precipitate is filtered off and then dried. Weight: 1.20 g—yield=39%—yellow powder—m.p.=275° C.

Analysis in agreement for $C_{26}H_{23}N_5O_3$—TLC: S.A6; 0.40 $^1H$ NMR δ (ppm): 2.20 (s, 3H); 3.00–3.10 (m, 1H); 3.20–3.30 (m, 1H); 3.70–3.80 (m, 2H exch.); 3.85–4.00 (m, 1H); 4.55–4.70 (m, 1H); 5.55 (d, 1H); 6.50 (s, 1H); 6.85 (s, 1H); 7.30–7.60 (m, 7H); 7.85 (d, 1H); 8.10 (d, 1H); 8.60 (d, 1H), 11.00 (m, 1H) I.R.: 3300, 1690, 1640, 1500, 1440, 1370, 1300, 1270, 1240, 1190, 1100, 960, 850, 750, 700 $cm^{-1}$.

Example 7

(3R)-N-(9-Amino-4-oxo-1-phenyl-3,4,6,7-tetrahydror[1,4]diazepino[6,7,1-hi]indol-3-yl)-2-methoxybenzamide

[($I_e$); A=2-methoxyphenyl; B=—$NR_2R_3$; $R_2$=$R_3$=H]

The compound is prepared according to the procedure of Example 2, starting with the intermediate amine 2 and 2-methoxybenzoic acid. The product is purified by flash chromatography on a column of silica, eluting with the mixture S.A8. After evaporation of the solvents, the purified product is solidified in ethyl ether.

Yield=65.5%—yellow powder—m.p.=234° C.—$[\alpha]_D$=+39.5° (c=1, $CH_2Cl_2$) Analysis in agreement for $C_{25}H_{22}O_3N_4$—TLC: S.A3; 0.60 $^1H$ NMR δ (ppm): 3.00–3.10 (m, 1H); 3.15–3.30 (m, 1H); 3.75 (m, 2H); 3.95 (q, 1H); 4.05 (s, 3H); 4.55–4.70 (m, 1H); 5.65 (d, 1H); 6.45 (s, 1H); 6.85 (s, 1H); 7.00 (d, 1H); 7.10 (t, 1H); 7.35 (t, 2H); 7.40–7.55 (m, 2H); 7.60 (d, 2H); 8.25 (d, 1H); 9.85 (d, 1H). I.R.: 3300, 1670, 1640, 1600, 1500, 1480, 1470, 1240, 1160, 1020, 750, 700 $cm^{-1}$.

Example 8

(3R)-4-Amino-N-(9-amino-4-oxo-1-phenyl-3,4,6,7-tetrahydro[1,4]diazepino[6,7,1-hi]indol-3-yl)-5-chloro-2-methoxybenzamide

[($I_e$); A=4-amino-5-chloro-2-methoxyphenyl; B=$NR_2R_3$; $R_2$=$R_3$=H]

The compound is prepared according to the procedure of Example 2, starting with the intermediate amine 2 and 4-amino-5-chloro-2-methoxybenzoic acid. The product is purified by flash chromatography on a column of silica, eluting with a mixture of dichloromethane progressively enriched with methanol.

Yield=38%—yellow powder—m.p.=198–200° C.—$[\alpha]_D$=+36.50 (c=0.5, MeOH). Analysis in agreement for $C_{25}H_{22}ClN_5O_3$—TLC: S.A3; 0.50 $^1H$ NMR δ (ppm): 2.95–3.10 (s, 1H); 3.15–3.3 (m, 1H); 3.75 (s, 2H); 3.95 (s, 3H); 3.85–4.00 (m, 1H); 4.55 (s, 2H); 4.55–4.65 (m, 1H); 5.65 (d, 1H); 6.35 (s, 1H); 6.55 (d, 1H); 6.80 (s, 1H); 7.30–7.45 (m, 3H); 7.55 (d, 2H); 8.15 (s, 1H); 9.65 (d, 1H).

I.R.: 3300, 1660, 1620, 1580, 1470, 1370, 1300, 1240, 1160, 1110, 1040, 980, 700 cm$^{-1}$.

Example 9

(3R)-N-(9-Amino-4-oxo-1-phenyl-3,4,6,7-tetra-hydro[1,4]diazepino[6,7,1-hi]indol-3-yl)-3-cyclopentyloxy- 4-methoxybenzamide

[(I$_e$); A=3-cyclopentyloxy-4-methoxyphenyl; B=NR$_2$R$_3$; R$_2$=R$_3$=H]

Compound prepared according to the procedure of Example 2, starting from the intermediate amine 2 and 3-cyclopentyloxy-4-methoxybenzoic acid (prepared according to J. Med. Chem. 1994., 37, 1696–1703). After purification by flash chromatography on a column of silica, eluting with ethyl acetate, the product is finally solidified by dissolution in ethyl acetate and then precipitation with hexane.

Yield=63%—yellow powder—m.p.=138–146° C.—[α]$_D$=+48° (c=1, CH$_2$Cl$_2$). Analysis in agreement for C$_{30}$H$_{30}$N$_4$O$_4$—TLC: S.B; 0.40 $^1$H NMR δ (ppm): 1.55–1.70 (m, 2H); 1.75–2.10 (m, 6H); 2.95–3.10 (m, 1H); 3.20–3.35 (m, 1H); 3.80 (5, 2H); 3.90 (s, 3H); 3.90–4.00 (m, 1H); 4.55–4.70 (m, 1H); 4.85–4.95 (m, 1H); 5.55–5.65 (d, 1H); 6.45 (d, 1H); 6.80–7.00 (m, 2H); 7.30–7.65 (m, 7H), 7.90–8.00 (d, 1H) I.R.: 3320, 2920, 1650, 1480, 1370, 1260, 1160, 1020, 760, 700, 520 cm$^{-1}$.

Example 10

(3R)-Pyridine-2-carboxylic acid (9-amino-4-oxo-1-phenyl-3,4,6,7-tetrahydro[1,4]diazepino[6,7,1-hi]indol-3-yl)amide

[(I$_e$); A=2-pyridyl; B=—NR$_2$R$_3$; R$_2$=R$_3$=H]

Preparation according to the procedure of Example 2, starting with the intermediate amine 2 and picolinic acid (or 2-pyridinecarboxylic acid). The product is purified by recrystallization from isopropanol.

Yield=50%—yellow powder—m.p.=266–267° C.—[α]$_D$=+67° (c=1, CH$_2$Cl$_2$) Analysis in agreement for C$_{23}$H$_{19}$N$_5$O$_2$—TLC: S.A2; 0.45 $^1$H NMR δ (ppm): 2.95–3.10 (m, 1H); 3.15–3.35 (m, 1H); 3.70–3.85 (s, 2H); 3.85–4.00 (m, 1H); 4.55–4.70 (m, 1H); 5.55–5.70 (d, 1H); 6.45 (s, 1H); 6.85 (s, 1H); 7.30–7.70 (m, 6H); 7.80–7.90 (m, 1H); 8.15–8.30 (m, 1H); 8.60–8.70 (m, 1H); 9.60–9.80 (d, 1H) I.R.: 3320, 1660, 1500, 1370, 1270, 1230, 1170, 995, 830, 690 cm$^{-1}$.

Example 11

(3R)-N-(9-amino-4-oxo-1-phenyl-3,4,6,7-tetrahydro [1,4]diazepino[6,7,1-hi]indol-3-yl)nicotinamide

[(I$_e$); A=3-pyridyl; B=NR$_2$R$_3$; R$_2$=R$_3$=H]

Preparation according to the procedure of Example 10 above with the intermediate amine 2 and nicotinic acid (or 3-pyridinecarboxylic acid). After purification by chromatography, eluting with the mixture S.A9, the product is crystallized from methanol.

Yield=33%—yellow powder—m.p. =>250° C. Analysis in agreement for C$_{23}$H$_{19}$N$_5$O$_2$-(0.4 HeOH)—TLC: S.A1; 0.50 $^1$H NMR δ (ppm): 2.95–3.10 (m, 1H); 3.20–3.30 (m, 1H); 3.80–3.90 (m, 1H); 4.40–4.50 (m, 1H); 5.30 (s, 2H); 5.55 (d, 1H); 6.35 (s, 1H); 6.90 (s, 1H); 7.40–7.60 (m, 6H); 8.35–8.40 (m, 1H); 8.75 (d, 1H); 9.15 (s, 1H); 9.90 (d, 1H) I.R.: 3300, 3200, 1660, 1580, 1460, 1380, 1265, 1235, 1165, 1020, 840, 695 cm$^{-1}$.

Example 12

(3R)-N-(9-Amino-4-oxo-1-phenyl-3,4,6,7-tetra-hydro[1,4]diazepinor [6,7,1-hi]indol-3-yl)-isonicotinamide

[(I$_e$); A=4-pyridyl; B=—NR$_2$R$_3$; R$_2$=R$_3$=H]

Preparation according to the procedure of Example 10 with the intermediate amine 2 and isocotinic [sic] acid (or 4-pyridinecarboxylic acid). After purification by chromatography, eluting with the mixture S.A10, the product is solidified in diethyl ether.

Yield=41%—yellow powder—m.p.=>280° C.—[α]$_D$=+60.80 (c=1, MeOH) Analysis in agreement for C$_{23}$H$_{19}$N$_5$O$_2$—TLC: S.A1; 0.50 $^1$H NMR δ (ppm): 2.95–3.08 (m, 1H); 3.20–3.30 (m, 11); 3.80–3.90 (m, 1H); 4.35–4.48 (m, 1H); 5.25 (s, 2H exch.); 5.45 (d, 1H); 6.00 (s, 1H); 6.90 (s, 1H); 7.40–7.60 (m, 5H); 7.95 (d, 2H); 8.80 (d, 2H); 9.90 (d, 1H) I.R.: 3300, 3200, 1660, 1480, 1380, 1240, 1170, 1060, 840, 695, 780, 750, 690 cm$^{-1}$.

Example 13

(3R)-3-t-Butyloxycarbonylamino-N-(9-amino-4-oxo-1-phenyl-3,4,6,7-tetrahydro[1,4]diazepino[6,7,1-hi]indol-3-yl)isonicotinamide

[(I$_e$); A=2-butyloxycarbonylamino-4-pyridyl; B=—NR$_2$R$_3$; R$_2$=R$_3$=H]

0.50 g (1.7 mmol) of the intermediate amine 2 and 0.41 g (1.7 mmol) of 3-t-butyloxycarbonylaminopyridine-4-carboxylic acid, prepared by reacting 3-aminoisonicotinic acid with di-t-butyl dicarbonate in dioxane, are dissolved in 10 ml of anhydrous tetrahydrofuran, in a reactor protected from moisture and under a nitrogen atmosphere.

0.96 g (2.05 mmol) of PyBrop (bromo-tris-pyrrolidino-phosphonium hexafluorophosphate) and 0.52 g (5.1.mmol) of triethylamine are then added with stirring at 20–25° C.

The mixture is stirred for 16 hours at 20–25° C., the insoluble material is filtered off and discarded and the filtrate is concentrated under vacuum on a water bath.

The residue is purified by flash chromatography on a column of silica. Elution with the mixture S.A8 allows 0.55 g of purified product to be obtained.

Yield=63%—yellow crystallized powder—m.p.=221–225° C.—[α]$_D$=-24.50 (c=0.5, CH$_2$Cl$_2$) Analysis in agreement for C$_{28}$H$_{28}$N$_6$O$_4$—(0.6 H$_2$O)—TLC: S.A1; 0.70 $^1$H NMR δ (ppm): 1.4 (s, 9H); 2.95–3.10 (m, 1H); 3.30–3.45 (m, 1H); 3.85 (q, 1H); 4.40 (t, 1H); 5.30 (s, 2H); 5.40 (d, 1H); 6.35 (d, 1H); 6.90 (d, 1H); 7.35–7.60 (m, 5H); 7.90 (d, 1H); 8.40 (d, 1H); 9.45 (s, 1H); 9.90 (s, 1H); 10.05 (d, 1H). I.R.: 3350, 1720, 1650, 1560, 1510, 1410, 1370, 1240, 1150, 1050, 1020, 700 cm$^{-1}$.

Example 14

(3R)-3-Amino-N-(9-amino-4-oxo-1-phenyl-3,4,6,7-tetrahydro[1,4]diazepino[6,7,1-hi]indol-3-yl) isonicotinamide

[(I$_e$); A=2-amino-4-pyridyl; B=—NR$_2$R$_3$; R$_2$=R$_3$=H]

0.55 g (1.07 mmol) of the (3R)-3-t-butyloxycarbonylamino-N-(9-amino-4-oxo-1-phenyl-3,4,6, 7-tetrahydro-[1,4]diazepino[6,7,1-hi]indol-3-yl) isonicotinamide obtained in the above example is dissolved in 20.0 ml of anhydrous dichloromethane in a reactor. 4.27 g (37.5 mmol) of pure trifluoroacetic acid (d=1.480) are added dropwise with stirring at 20–25° C. After stirring for 30 minutes at 20–25° C., the mixture is concentrated by distillation under vacuum on a water bath. The residue is dissolved in 25 ml of ethyl acetate and the solution is washed with twice 10 ml of saturated sodium bicarbonate solution and then dried. The solvent is eliminated by distillation under vacuum and the residue is purified by flash chromatography on silica. Elution with dichloromethane progressively enriched with methanol allows 0.17 g of the correct purified product to be obtained.

Yield=38%—yellow crystallized powder—m.p.= 215–230° C.—$[\alpha]_D$=−4.35° (c0.5, $CH_2Cl_2$) Analysis in agreement for $C_{23}H_{20}N_6O_2$ (0.3 $CH_2Cl_2$) (0.8 $H_2O$ )—TLC: S.A1; 0.55 $^1H$ NMR (ppm): 2.95–3.10 (m, 1H); 3.20–3.35 (m, 1H); 3.30–4.10 (m, 2H); 3.85–4.00 (q, 1H); 4.50–4.70 (t, 1H); 5.55 (d, 1H); 6.45 (s, 1H); 6.85 (s, 1H); 7.30–7.50 (m, 4H); 7.50–7.65 (m, 2H); 7.95 (d, 1H); 8.05–8.25 (m, 2H). I.R.: 3300, 1640, 1580, 1480, 1370, 1230, 1050, 780, 700 $cm^{-1}$.

Example 15

(3R)-3-Acetylamino-N-(9-acetylamino-4-oxo-1-phenyl-3,4,6,7-tetrahydro[1,4]diazepino[6,7,1-hi] indol-3-yl)isonicotinamide

[($I_{eb}$); A=2-acetylamino-4-pyridyl; B=—$NR_2R_3$; $R_2$=$R_4$=—CO—$CH_3$; $R_3$=H]

0.130 g (0.315 mmol) of (3R)-3-amino-N-(9-amino-4-oxo-1-phenyl-3,4,6,7-tetrahydro[1,4]diazepino[6,7,1-hi] indol-3-yl)isonicotinamide obtained in the above example, 1.3 ml of anhydrous pyridine and 0.69 g (6.75 mmol) of acetic anhydride are introduced into a round-bottomed flask protected from moisture.

The mixture is stirred for 16 hours at 20–25° C., 6.5 ml of water are then added and stirring is continued for 5 hours, the mixture is extracted with twice 15 ml of ethyl acetate and the combined organic phases are washed with saturated sodium bicarbonate solution and then dried. The ethyl acetate is eliminated by distillation and the residue is then purified by flash chromatography on silica.

Elution with dichloromethane progressively enriched with methanol allows 0.050 g of purified product to be obtained.

Yield=32% —pale-yellow amorphous powder Analysis in agreement for $C_{27}H_{24}O_4N_6$ [sic]—TLC: S.A1; 0.52 $^1H$ NMR δ (ppm): 2.10 (s, 3H); 2.15 (s, 3H); 3.20–3.05 (m, 1H); 3.25–3.45 (m, 1H); 3.95 (q, 1H); 4.60 (t, tH); 5.50 d, 1H); 7.15 (s, 1H); 7.35 (t, 2H); 7.40 (t, 1H); 7.45 (d, 2H); 7.55 (d, 1H); 7.90 (s, 1H); 8.30 (d, 1H); 8.45 d, 1H); 8.55 (s, 1H); 9.75 (s, 1H); 10.45 (s, 1H).

Example 16

(3R)-N-(9-Amino-4-oxo-1-phenyl-3,4,6,7-tetrahydror[1,4]diazepino[6,7,1-hi]indol-3-yl)-3,5-dichloroisonicotinamide

[($I_e$); A=3,5-dichloro-4-pyridyl; B=—$NR_2R_3$; $R_2$=$R_3$=H]

The compound is prepared according to the procedure of Example 2, starting with the intermediate amine 2 and 3,5-dichloropyridine-4-carboxylic acid.

The product is purified by chromatography, the elution being performed with the mixture S.A8. The product is finally crystallized from an ethyl acetate/hexane mixture.

Yield=32%—yellow powder—m.p.=165–166° C.—$[\alpha]_D$=+175° (c=1, $CH_2Cl_2$). Analysis in agreement for $C_{23}H_{17}Cl_2N_5O_2$—(0.4 EtOAc)—TLC: S.A3; 0.60. $^1H$ NMR δ (ppm): 3.00–3.15 (m, 1H); 3.25–3.40 (m, 1H); 3.70–3.85 (s, 2H); 3.85–4.00 (m, 1H); 4.55–4.70 (m, 1H); 5.60–5.70 (d, 1H); 6.50 (s, 1H); 6.85 (s, 1H); 7.35–7.65 (m, 5H); 7.80–7.95 (d, 1H); 8.60 (s, 2H). I.R.: 3320, 1660, 1560, 1370, 1230, 1200, 1090, 1030, 820, 700 $cm^{-1}$.

Example 17

(3R)-Pyrazine-2-carboxylic acid (9-amino-4-oxo-1-phenyl-3,4,6,7,-tetrahydro[1,4]diazepino[6,7,1-hi] indol-3-yl)amide

[($I_e$); A=2-pyrazyl; B=—$NR_2R_3$; $R_2$=$R_3$=H]

Compound prepared according to the procedure of Example 2 with the intermediate amine 2 and pyrazine-2-carboxylic acid. The product is purified by flash chromatography and then crystallization from hexane.

Yield=59% —yellow powder—m.p.=264° C.—$[\alpha]_D$=+670 (c=1, $CH_2Cl_2$). Analysis in agreement for $C_{22}H_{18}N_6O_2$—TLC: S.A2; 0.40 $^1H$ NMR δ (ppm): 2.95–3.10 (m, 1H); 3.20–3.35 (m, 1H); 3.80–3.95 (m, 1H); 4.35–4.50 (m, 1H); 5.30–5.40 (m, 3H); 6.40 (d, 1H); 6.85 (d, 1H); 7.40–7.55 (m, 5H); 8.80–9.00 (m, 2H); 9.30 (s, 1H); 9.40–9.50 (d, 1H). I.R.: 3350, 2900, 1670, 1500, 1370, 1170, 1040, 850, 690, 530 $cm^{-1}$.

Example 18

(3R)-Isoquinoline-3-carboxylic acid (9-amino-4-oxo-1-phenyl-3,4,6,7-tetrahydro[1,4]-diazepino[6,7,1-hi]indol-3-yl)amide

[($I_e$); A=3-isoquinolyl; B=—$NR_2R_3$; $R_2$=$R_3$=H]

Compound prepared according to the procedure of Example 2 with the intermediate amine 2 and isoquinoline-3-carboxylic acid. The purified product is obtained by crystallization and flash chromatography on silica with the elution mixture S.A8.

Yield=55%—yellow powder—m.p.=>282° C.—$[\alpha]_D$=+16° (c=1, $CH_2Cl_2$). Analysis in agreement for $C_{27}H_{21}N_5O_2$—TLC: S.A3; 0.80 $^1H$ NMR δ (ppm): 3.00–3.10 (m, 1H); 3.20–3.30 (m, 1H); 3.80–3.90 (m, 1H); 4.40–4.50 (m, 1H); 5.30 (s, 2H); 5.40 (d, 1H); 6.40 (s, 1H); 6.90 (s, 1H); 7.40–7.55 (m, 5H); 7.20–7.95 (m, 2H); 8.20–8.35 (m, 2H); 8.65 (s, 1H); 9.5 (s, 1H), 9.65 (s, 1H). I.R.: 3300, 3200, 1670, 1500, 1380, 1300, 1270, 1230, 1160, 940, 935, 850, 740, 700 $cm^{-1}$.

Example 19

(3R)-Quinoline-3-carboxylic acid (9-amino-4-oxo-1-phenyl-3,4,6,7-tetrahydro[1,4]-diazepino[6,7,1-hi] indol-3-yl)amide

[($I_e$); A=3-quinolyl; B=—$NR_2R_3$; $R_2$=$R_3$=H]

Compound prepared according to the procedure of Example 2 with the intermediate amine 2 and quinoline-3-carboxylic acid. The product is purified by flash chromatography on silica, eluting with dichloromethane progressively enriched with methanol.

Yield=44% —yellow powder—m.p.=277° C.—$[\alpha]_D$=+75.5° (c=0.5, $CH_2Cl_2$). Analysis in agreement for $C_{27}H_{21}N_5O_2$ $^1H$ MMR δ (ppm): 3.00–3.15 (m, 1H); 3.20–3.40 (m, 1H); 4.3 (s, 2H); 3.95 (q, 1H); 4.60–4.70 (m, 1H); 5.65 (d, 1H); 6.50 (d, 1H); 6.85 (m, 1H); 7.55–7.30 (m, 3H); 7.60 (d, 2H); 7.65 (m, 1H); 7.85 (m, 1H); 7.95 (d, 1H); 8.15 (d, 1H); 8.75 (d, 1H); 8.75 (d, 1H); 9.45 (d, 1H). I.R.: 3300, 3200, 1650, 1620, 1500, 1480, 1240, 1220, 790, 760, 690 $cm^{-1}$.

Example 20

(3R)-4,7-Dimethylpyrazolo[5,1-c][1,2,4]triazine-3-carboxylic acid (9-amino-4-oxo-1-phenyl-3,4,6,7-tetrahydro[1,4]-diazepino[6,7,1-hi]indol-3-yl)amide

[($I_e$); A=4,7-dimethylpyrazolo[5,1-c][1,2,4]-3-triazinyl; B=—$NR_2R_3$; $R_2$=$R_3$=H]

Compound prepared according to the procedure of Example 2 and starting with the intermediate 2 of [sic] 4,7-dimethylpyrazolo[5,1-c[1,2,4]triazine-3-carboxylic [sic] acid. The product is purified by flash chromatography on silica, eluting with dichloromethane progressively enriched with methanol.

Yield=40%—orange-yellow powder—m.p.=168–170° C.—Analysis in agreement for $C_{25}H_{22}N8O_2$—(0.5 120)—TLC: S.A3; 0.60 $^1$H NMR δ (ppm): 2.65 (s, 3H); 3.00–3.15 (m, 1H); 3.25–3.35 (m, 1H); 3.30 (s, 3H), 3.70–3.80 (m, 2H); 3.95 (q, 1H); 4.55–4.75 (m, 1H); 5.65 (d, 1H); 6.50 (d, 1H); 6.85 (d, 1H); 7.10 (s, 1H); 7.35–7.45 (m, 3H); 7.60 (d, 2H); 9.85 (d, 1H). I.R.: 3300, 1660, 1560, 1480, 1370, 1300, 1240, 1160, 850, 780, 700 cm$^{-1}$.

Example 21

(3R)-4-Amino-3,5-dichloro-N-(9-dimethylamino-4-oxo-1-phenyl-3,4,6, 7-tetrahydro[1,4]-diazepino[6,7, 1-hi]indol-3-yl)benzamide

[($I_{ed}$); A=4-amino-3,5-dichlorophenyl; B=—NR$_2$R$_3$; R$_2$=R$_3$ =CH$_3$]

2.00 g (4.2 mmol) of (3R)-4-amino-N-(9-amino-4-oxo-1-phenyl-3,4,6,7-tetrahydro[1,4]diazepino[6,7,1-hi]indol-3-yl)-3,5-dichlorobenzamide (product of Example 4) are dissolved in 100 ml of acetonitrile in a 250 ml reactor.

3.43 ml of 37% formaldehyde solution (42 mmol) are added at 20–25° C. with stirring, followed by 0.80 g (12.5 mmol) of sodium cyanoborohydride and 0.50 ml of pure acetic acid. The mixture is stirred for two hours at room temperature, followed by addition of a further 0.50 ml of acetic acid, after which the mixture is stirred for 15 minutes and is then precipitated in 350 ml of ethyl ether.

The white precipitate which forms is filtered off and discarded and the filtrate is extracted with twice 100 ml of N NaOH solution. The ether phase is washed with saturated NaCl solution and then dehydrated. The ethyl ether is eliminated by distillation and the residue is purified by flash chromatography on silica. Elution with dichloromethane progressively enriched with acetone leads to the recovery of 0.80 g of purified product, which is solidified in an ethyl ether/heptane mixture. The product is filtered off and then dried. Weight 0.75 g.

Yield=35%—orange-yellow powder—m.p. =174–176° C. Analysis in agreement for $C_{26}H_{23}Cl_2N_5O_2$—(0.3 H$_2$O)—TLC: S.A3; 0.75 $^1$H NMM δ (ppm): 2.90 (s, 6H); 3.00–3.15 (m; 1H); 3.25–3.40 (m, 1H); 3.95 (q, 1H); 4.65 (t, 1H); 4.85 (s, 2H); 5.60 (d, 1H); 6.45 (d, 1H); 6.95 (s, 1H); 7.35 (t, 2H); 7.40–7.50 (m, 1H); 7.60 (d, 2H); 7.80–7.95 (m, 3H). I.R.: 3300, 1650, 1610, 1470, 1370, 1270, 1220, 1120, 780, 700 cm$^{-1}$.

Example 22

(3R)-4-Amino-3,5-dichloro-N- (4-oxo-1-phenyl-9-pyrrolidin-1-yl-3,4,6,7-tetrahydro[1,4]-diazepino[6, 7,1-hi]indol-3-yl)benzamide

[($I_{ee}$); A=4-amino-3,5-dichlorophenyl; B=—NR$_2$R$_3$; R$_2$—R$_3$=—(CH$_2$)$_4$—]

3.00 g (6.0 mmol) of (3R)-4-amino-N-(9-amino-4-oxo-1-phenyl-3,4,6,7-tetrahydro[1,4]diazepino[6,7,1-hi]indol-3-yl)-3,5-dichlorobenzamide (product of Example 4) are dissolved in 100 ml of acetonitrile in a 250 ml round-bottomed flask. 1.48 g (6.9 mmol) of 1,4-dibromobutane are added and the mixture is maintained at reflux with stirring for 16 hours. The acetonitrile is eliminated by distillation under vacuum and the residue is taken up in 250 ml of water and basified with soda lye. The mixture is extracted with 3 times 100 ml of dichloromethane, the combined organic phases are washed and then dried and the solvent is eliminated by distillation. The residue is purified by flash chromatography on a column of silica, eluting with dichloromethane progressively enriched with acetone. Weight: 0.75 g. Yield= 7.5%.

Analysis in agreement for $C_{28}H_{25}Cl_2N_5O_2$—TLC: S.A6; 0.85 $^1$H NMR δ (ppm): 1.90–2.05 (m, 4H); 3.00–3.10 (m, 1H); 3.15–3.25 (m, 4H); 3.25–3.40 (m, 1H); 3.95 (q, 1H); 4.60 (t, 1H); 4.80 (s, 2H); 5.50 (d, 1H); 6.25 (s, 1H); 6.75 (s, 1H); 7.30–7.50 (m, 3H); 7.60 (d, 2H); 7.80–7.95 (m, 3H). I.R.: 3300, 1650, 1610, 1470, 1380, 1270, 890, 780, 700 cm$^{-1}$.

Example 23

(3R)-4-Amino-3,5-dichloro-N-(4-oxo-1-phenyl-9-morpholin-1-yl-3,4,6,7-tetrahydro[1,4]-diazepino[6, 7,1-hi]indol-3-yl)benzamide

[($I_{ee}$); A=4-amino-3,5-dichlorophenyl; B=—NR$_2$R$_3$; R$_2$—R$_3$ =—(CH$_2$)$_2$—O—(CH$_2$)$_2$—]

The compound is prepared according to the procedure of Example 22 above, starting with 1.0 g (2.1 mmol) of (3R)-4-amino-N-(9-amino-4-oxo-1-phenyl-3,4,6,7-tetrahydro[1,4]diazepino[6,7,1-hi]indol-3-yl)-3,5-dichlorobenzamide (product of Example 4) in 35 ml of acetonitrile and 0.67 g (3.1 mmol) of 2-dibromoethyl ether. The product is purified by flash chromatography.

TLC: S.A6; 0.55. $^1$H NMR δ (ppm): 2.90–3.10 (m, 5H); 3.20–3.35 (m, 1H); 3.70–3.80 (m, 4H); 3.90 (q, 1H); 4.60 (t, 1H); 4.75 (s, 2H); 5.50 (d, 1H); 6.60 (s, 1H); 7.05 (s, 1H); 7.30–7.45 (m, 3H); 7.50 (d, 2H); 7.75 (d, 1H); 7.80 (s, 2H).

Example 24

(3R)-4-Amino-3,5-dichloro-N-(9-guanidino-4-oxo-1-phenyl-3,4,6,7-tetrahydro[4,1]-diazepino[6,7,1-hi] indol-3-yl)benzamide

[($I_{ea}$); A=4-amino-3,5-dichlorophenyl; B=—NR$_2$R$_3$; R$_2$=—C(NH) NH$_2$R$_3$=H]

2.02 g (4.2 mmol) of (3R)-4-amino-N-(9-amino-4-oxo-1-phenyl-3,4,6,7-tetrahydro[1,4]diazepino[6,7,1-hi]indol-3-yl)-3,5-dichlorobenzamide dissolved in 50 ml of dichloromethane are introduced into a 250 ml reactor. 5 ml of 4N hydrochloric ether are added and the solvents are then evaporated off under vacuum.

The residue is taken up, with stirring, in 150 ml of acetonitrile and 0.192 g (4.6 mmol) of cyanamide is added at 20–25° C. with stirring. The suspension is heated and maintained at reflux for 41 hours with stirring. After cooling to about 10° C., the insoluble material is filtered off and taken up in 25 ml of water. The mixture is basified with 10 N soda lye and extracted with twice 50 ml of dichloromethane. The combined organic phases are washed and dried and the solvent is then eliminated by distillation. The crude product (1.0 g) is purified by flash chromatography on silica. Elution with a mixture of dichloromethane and 10% ammoniacal methanol in a proportion of 50/50 allows the expected product to be purified. Weight=0.27 g.

Yield=13%—pale yellow powder—m.p.=>220° C. Analysis in agreement for $C_{25}H_{21}Cl_2N_7O_2$—(4 H$_2$O)—TLC: S.C; 0.20 $^1$H NMR δ (ppm): 3.00–3.15 (m, 1H); 3.20–3.35 (m, 1H); 3.90 (q, 1H); 4.45 (t, 1H); 5.45 (d, 1H); 6.80 (s, 1H); 7.30 (s, 1H); 7.40 (t, 2H); 7.45–7.60 (m, 3H); 8.00 (s, 2H) 8.65 (s, 2H); 9.55 (d, 1H).

Example 25

(3R)-N-(9-Acetylamino-4-oxo-1-phenyl-3,4,6,7-tetrahydro[1,4]diazepino[6,7,1-hi]indol-3-yl)-4-amino-3,5-dichlorobenzamide

[($I_{eb}$); A=4-amino-3,5-dichlorophenyl; B=—NR$_2$R$_3$; R$_2$=—C(O)CH$_3$; R$_3$=H]

2.50 g (3.12 imol) of (3R)-4-amino-N-(9-amino-4-oxo-1-phenyl-3,4,6,7-tetrahydro[1,4]diazepino[6,7,1-hi]indol-3- yl)-3,5-dichlorobenzamide dissolved in 12.85 ml of anhydrous pyridine are introduced into a 25 ml round-bottomed flask, followed by addition of 6.70 g, i.e. 6.2 ml (6.56 mmol) of acetic anhydride. The solution is stirred for 16 hours at 20–25° C., 65 ml of water are then added and the mixture is left stirring for 4 hours at room temperature. The mixture is next extracted with 3 times 75 ml of ethyl acetate and the combined organic phases are washed with saturated sodium bicarbonate solution and then dried and evaporated under vacuum. The residue is purified by flash chromatography on a column of silica, eluting with dichloromethane progressively enriched with methanol. The purified residue, weighing 2.0 g, is taken up in ethyl acetate and washed with HCl and then with water in order to remove the residual pyridine.

Weight: 0.70 g—yield=43% m.p.=192° C.—Analysis in agreement for $C_{26}H_{21}Cl_2N_5O_3$—(0.6 $H_2O$)—TLC: S.A1; 0.75 $^1$H NMR δ (ppm): 2.10 (s, 3H); 3.00–3.15 (m, 1H); 3.20–3.35 (m, 1H); 3.95 (q, 1H); 4.60 (t, 1H); 4.85 (s, 2H); 5.35 (d, 1H); 7.00 (s, 1H); 7.25–7.50 (m, 5H); 7.80 (s, 2H); 7.85 (d, 1H); 7.95 (s, 1H) 8.35 (s, 1H) I.R.: 3300, 1660, 1610, 1540, 1470, 1370, 1270, 780, 700 $cm^{-1}$.

Example 26

(3R)-4-Amino-3,5-dichloro-N-(9-{2-[2-(2-methoxyethoxy)ethoxy]acetylamino}-4-oxo-1-phenyl-3,4,6 7-tetrahydro[1,4]diazepino-[6,7,1-hi]indol-3-yl)benzamide

[($I_{eb}$); A=4-amino-3,5-dichlorophenyl; B=—$NR_2R_3$; $R_2$=$CH_3$—(O—$CH_2$—$CH_2$)$_2$—O—$CH_2$—CO; $R_3$=H]

The compound is prepared according to the procedure of Example 2, starting with (3R)-4-amino-N-(9-amino-4-oxo-1-phenyl-3,4,6,7-tetrahydro[1,4]diazepino[6,7,1-hi]indol-3-yl)-3,5-dichlorobenzamide (product of Example 4) and 3,6,9-trioxodecanoic acid.

The product is purified by flash chromatography on silica, eluting with dichloromethane progressively enriched with acetone.

Yield=45%—white powder—m.p.=105–107° C.—Analysis in agreement for $C_{31}H_{31}Cl_2N_5O_6$—(0.55 $H_2O$)—TLC: S.A6; 0.25 $^1$H NMR δ (ppm): 3.05–3.20 (m, 1H); 3.25 (s, 3H); 3.30–3.40 (m, 3H); 3.45–3.60 (m, 2H); 3.60–3.80 (m, 4H); 4.00 (q, 1H); 4.10 (d, 2H); 4.65 (t, 1H); 4.85 (s, 2H); 6.45 (d, 1H); 7.20 (d, 1H); 7.30–7.45 (m, 2H); 7.45–7.50 (m, 1H); 7.55 (dd, 2H); 7.80–7.90 (m, 3H); 8.10 (s, 1H); 8.95 (s, 1H). I.R.: 3250, 2850, 1670, 1610, 1520, 1460, 1370, 1270, 1100, 780 $cm^{-1}$.

Example 27

(3R)-(2-{2-[3-(4-Amino-3,5-dichlorobenzoyl-amino)-4-oxo-1-phenyl-3,4,6 7-tetrahydro-[1,4] diazepino[6,7,1-hi]indol-9-ylcarbamoyl-methoxy]ethoxy}ethoxy)acetic acid

[($I_{eb}$); A=4-amino-3,5-dichlorophenyl; B=—$NR_2R_3$; $R_2$=HOOC—$CH_2$—(O—$CH_2$—$CH_2$)$_2$—O—$CH_2$—CO; $R_3$=H]

The compound is prepared according to Example 23 above with 3,6,9-trioxaundecanedioic acid. The product is purified by chromatography followed by solidification in diethyl ether.

Yield=30%—pale yellow powder—m.p.=>230° C.—Analysis in agreement for $C_{32}H_{31}Cl_2N_5O_8$—(1 $H_2O$)—TLC: S.C; $^1$H NMR δ (ppm): 3.05–3.20 (m, 1H); 3.35–3.45 (m, 1H); 3.45–3.65 (m, 9H); 3.70 (s, 2H); 3.90 (q, 1H); 4–10 (s, 2H); 4.40 (t,. 1H); 5.45 (d, 1H); 6.65 (s, 2H); 7.40–7.60 (m, 6H); 7.95 (s, 1H); 8.00 (s, 2H); 9.55 (d, 1H); 10.15 (s, 1H); I.R.: 3250, 1610, 1520, 1460, 1370, 1270, 1100, 780, 700 $cm^{-1}$.

Example 28

(3R)-Hexadecanoic acid [3-(4-amino-3,5-dichlorobenzoylamino)-4-oxo-1-phenyl-3,4,6,7-tetrahydro[1,4]diazepino[6,7,1-hi]indol-9-ylamide

[($I_{eb}$); A=4-amino-3,5-dichlorophenyl; B=—$NR_2R_3$; $R_2$=$CH_3$—($CH_2$)$_{14}$—CO; $R_3$=H]

1.00 g (2.1 mmol) of (3R)-4-amino-N-(9-amino-4-oxo-1-phenyl-3,4,6,7-tetrahydro[1,4]diazepino[6,7,1-hi]indol-3-yl)-3,5-dichlorobenzamide (product of Example 4) is dissolved in 10.0 ml of anhydrous pyridine in a 25 ml round-bottomed flask under a nitrogen atmosphere. 0.63 g (2.3 mmol) of hexadecanoyl chloride (or palmitoyl chloride) is then added at 20–25° C. The solution is kept stirring at 20–25° C. for 2 h 30 and is then concentrated under vacuum. The residue is taken up in 50 ml of 1/1 (v/v) dichloromethane/diethyl ether mixture. The organic phase is washed with 3 times 25 ml of N HCl solution and then successively with 3 times 25 ml of 10% NaOH solution and 3 times 25 ml of water, after which it is dried and the solvents are eliminated by distillation.

The residue is solidified in heptane, filtered off and dried. Weight: 0.90 g

Yield=60%—white powder—m.p.=130° C.—Analysis in agreement for $CH_{40}H_{49}Cl_2N_5O_3$—TLC: S.A; 0.85 $^1$H NMR δ (ppm): 0.85 (t, 3H); 1.25 (s, 24H); 1.50–1.70 (m, 2H); 2.25 (t, 2H); 3.05–3.15 (m, 1H); 3.20–3.35 (m, 1H); 3.95 (q, 1H); 4.60 (t, 1H); 4.85 (s, 2H); 5.35 (d, 1H); 7.00 (s, 1H); 7.25–7.35 (m, 2H); 7.40 (d, 1H); 7.45 (d, 2H); 7.75–7.90 (m, 3H); 7.95 (d, 2H). I.R.: 3250, 2900, 2800, 1660, 1610, 1530, 1460, 1370, 1270, 1230, 1120, 880, 780 $cm^{-1}$.

Example 29

(3R)-Isoauinoline-3-carboxylic acid (9-acetylamino-4-oxo-1-phenyl-3 4,6,7-tetrahydro[1,4]diazepino[6,7,1-hi]indol-9-yl) amide

[($I_{eb}$); A=3-isoquinolyl; B=—$NR_2R_3$; $R_2$=$CH_3$—CO; $R_3$=H]

0.45 g (1.0 mmol) of (3R)-isoquinoline-3-carboxylic acid (9-amino-4-oxo-1-phenyl-3,4,6,7-tetrahydro-[1,4]diazepino [6,7,1-hi]indol-3-yl)amide (product of Example 18) is dissolved in 10.0 ml of anhydrous pyridine in a 50 ml round-bottomed flask under a nitrogen atmosphere. 3.0 ml (30 mmol) of acetic anhydride are added, the mixture is stirred at 20–25° C. for 30 minutes and the medium is then precipitated in 100 ml of ice-water.

The solution is extracted with dichloromethane, the organic phase is washed with water and dried and the solvents are then eliminated by distillation under vacuum. The residue is taken up in 100 ml of ethyl ether and stirred at 10° C. for 30 minutes. The precipitate is filtered off and dried. Weight: 0.40 g.

Yield=82% —white powder—m.p.=280° C. Analysis in agreement for $C_{29}H_{23}N_5O_3$—TLC: S.A; 0.20 $^1$NMR δ (ppm): 2.10 (s, 3H); 3.00–3.10 (m, 1H); 3.20–3.30 (m, 1H); 3.85–3.95 (m, 1H); 4.50–4.60 (m, 1H); 5.50 (d, 1H); 7.10 (s, 1H); 7.20–7.40 (m, 4H); 7.50 (d, 1H); 7.70–7.80 (m, 2H); 7.95 (s, 1H); 8.00 (d, 1H); 8.10 (d, 1H); 8.60 (s, 1H); 8.75 (s, 1H); 9.30 (s, 1H); 9.8 (d, 1H). I.R.: 3300, 1650, 1490, 1380, 1250, 1160, 1050, 980, 860, 770, 750, 695 $cm^{-1}$.

Example 30

(3R)N-(9-amino-4-oxo-1-phenyl-3,4, 67-tetrahydro [1,4]diazepino[6,7,1-hi]indol-3-yl)-2-benzofuranecarboxamide

[($I_e$); A=2-benzofuranecarboxyl; B=—$NR_2R_3$; $R_2$=$R_3$=H]

Preparation according to the procedure of Example 10 starting with the intermediate amine 2 and benzofurane-2-carboxylic acid. After purification by chromatography eluting with dichloromethane progressively enriched with acetone and evaporation of the solvents, the product is obtained as an amorphous powder.

Yield=22%—pale yellow powder—F=>260° C. Analysis in agreement for $C_{26}H_{20}N_4O_3$ (0.25 $H_2O$) TLC: S.A10; 0.60 $^1$H NMR δ (ppm) : 3.00–3.15(m,1H); 3.20–3.40(m,1H) ;3.50–4.00(m,2H);3.95(q,1H);4.65(t,1H);5.65(d,1H);6.50(s, 1H); (6.85(s,1H);7.30(t,1H)7.35–7.40(m,2H);7,42–7,50(m, 2H);7.55(s,1H);7,60(d,3H);7.70(d,1H);8.45(d,1H) I.R. : 3200, 1650, 1590, 1470, 1440, 1370, 1270, 1170, 840, 750, 690 $cm^{-1}$.

Example 31

(3R)N-[4-oxo-1-phenyl-9-(pyrrolidin-1-yl)-3,4,6,7-tetrahydror[1,4]diazepino[6,7,1-hi]indol-3-yl)-isonicotinamide

[($I_{ee}$); A=4-pyridyl; B=—$NR_2R_3$; $R_2$-$R_3$=—$(CH_2)_4$—] 1.20 g (3.46 mmol) of (3R)3-amino-1-phenyl-9-pyrrolidin-1-yl)-6,7-dihydro-3H-[1,4]diazepino[6,7,1-hi]indol-4-one (IIf) intermediate 4 are dissolved in 24.0 ml anhydrous pyridine in a reactor protected from moisture. At a temperature <0° C., 0.92 g (5.17 mmol) of hydrochloride of isonicotinic acid chloride is added to the solution. The suspension is agitated for 48 hours at 20–25° C. under nitrogen atmosphere. 10 ml water and 10 ml dichloromethane are then added. The organic layer is separated, the aqueous phase is again extracted with dichloromethane. organic phases are put together, washed with water then dried. After evaporation of the solvents, the residue is purified by rapid chromatography on a column of silica. Elution by dichloromethane progressively enriched with methanol and elimination of the solvents yields a product in a pure state as a yellow amorphous powder.

Mass : 0.30 g—Yield : 19.2%—F=273° C. TLC=S.A10: 0.50 $^1$H NMR δ (ppm) : 2.00 (m,4H); 3.00 (m,1H); 3.20 (m,4H); 3.30 (m,1H); 3.90 (q,1H); 4.55 (q,1H); 5.50 (d,1H); 6.25 (s,1H); 6.70 (s,lH); 7.20–7.50 (m,3H); 7.60 (t,2H); 7.70 (d,2H); 8.00 (d,2H); 8.75 (d,2H). I.R. : 3040, 1640, 1480, 1380, 1240, 1160, 1060, 1020, 900, 880, 840, 700, 600 $cm^{-1}$.

Example 32

(3R) 4,7-dimethyl-pyrazolo[5,1-c][1,2,4]triazine-3-carboxylic acid [4-oxo-1-pheny-9-(pyrrolidin-1-yl)-3,4,6,7-tetrahydro[1,4]diazepino[6,7,1-hi]indol-3-yl)-amide

[($I_{ee}$); A=4,7-dimethyl-pyrazolo[5,1-c][1,2,4]-3-triazinyl, B=—$NR_2R_3$; $R_2$-$R_3$=—$(CH_2)_4$—]

Compound prepared according to the procedure of Example 2 starting with intermediate 4 from 4,7-dimethyl-pyrazolo[5,1-c][1,2,4]triazine-3-carboxylic acid. The product is purified by rapid chromatography on silica eluting with dichloromethane progressively enriched with methanol.

Yield : 20%—Yellow amorphous powder—F=>300° C. TLC=S.A8 : 0.20 $^1$H NMR δ (ppm) : 2.10 (m,4H); 2.60 (s,3H); 3.00 (m,1H); 3.15 (s,4H); 3.25 (s,3H); 3.30 (s,1H); 3.90 (q,1H); 4.60 (m,1H); 5.60 (d,lH); 6.25 (s,1H); 6.70 (s,1H); 7.00 (s,2H); 7.35 (m,3H); 7.60 (d,2H); 9.80 (d,1H) I.R. : 1660, 1560, 1450, 1360, 1240, 700 $cm^{-1}$.

BIOLOGICAL SECTION

Inhibitory activity of Phosphodiesterase

The capacity of the compounds of formula (I) of the invention to inhibit cyclic nucleotide phosphodiesterases is evaluated by measuring their $IC_{50}$ (concentration necessary to inhibit the enzymatic activity by 50%). In the case of PDEs 4, this value is compared to the $IC_{50}$ of rolipram, a PDE 4-specific inhibitor, relative to the $IC_{50}$ of rolipram on the $IC_{50}$ of the product to be tested with respect to the same enzymatic preparation.

The various types of phosphodiesterase are obtained partially purified on a DEAE-cellulose column from guinea pig trachea and dog aorta according to a method adapted from W. J. Thompson et al., 1979, Advances in Cyclic Nucleotide Research, Vol. 10: 69–92, ed. G. Brooker et al. Raven Press, New York, and from P. J. Silver et al., 1988, Eur. J. Pharmacol. 150: 85–94, and from the U937 cell line of human origin, according to a method adapted from T. J. Torphy et al., 1992, J. Pharm. Exp. Ther. 263: 1195–1205.

Measurement of the enzymatic activity for the various types of PDE, and in particular for the PDEs 4, is then made according to a method also adapted from W. J. Thompson, Ibidem.

In order to determine the $IC_{50}$, the enzymatic activity is measured in the presence of the inhibitor over a range of concentrations from 0.1 to 100 μM.

The following table illustrates the inhibitory activity of PDE 4 when compared with that of rolipram on an enzyme preparation obtained from the line U937.

| Ex. | $\frac{IC_{50} \text{ rolipram}}{IC_{50} \text{ example}}$ | Ex. | $\frac{IC_{50} \text{ rolipram}}{IC_{50} \text{ example}}$ |
|---|---|---|---|
| 1 | 1.9 | 18 | 11.0 |
| 4 | 33.0 | 19 | 1.4 |
| 8 | 3.4 | 20 | 1.1 |
| 12 | 2.0 | 21 | 3.3 |
| 12A (salt) | 5.7 | 30 | 15.0 |
| 13 | 1.6 | 32 | 4.0 |

Examination of the results from the above table shows that the products of the invention tested in the study generally inhibit the PDE 4 enzyme of human origin more effectively than rolipram, and, in certain cases, are about 30 times more active than rolipram.

Moreover, tests performed on different types of PDE, purified from guinea pig trachea or dog aorta, show that the $IC_{50}$ values obtained with the products of the invention with respect to PDEs of type 3 and of type 1 and 5 are much higher than those measured for the PDEs of type 4.

These results are strong evidence of a powerful and selective inhibitory activity of the products of the invention on PDEs 4.

Antiinflammatory and Antiallergic Activity in Vivo

The effects of the products of the invention were studied on guinea pigs in a model of eosinophil infiltration induced by antigen stimulation or by exposure to a PAF aerosol according to a methodology described by Lagente V. et al., (1994) Br. J. Pharmacol. 112, 83P.

The administration of products of the examples (1–30 mg/kg p.o.) significantly reduces the number of eosinophils in the broncho-alveolar washing liquid.

The administration of products of the invention also reduces the inflammatory responses induced by the intratracheal instillation of IL-5 in guinea pigs.

These results demonstrate the antiinflammatory and/or immunosuppressant activity of the products of the invention. The products of the invention will thus be particularly useful for the treatment or prevention:

of allergic pathologies, and in particular asthma and atopic dermatitis;

inflammatory pathologies, in particular bronchial pathologies, but also rheumatoid arthritis, and also inflammatory intestinal complaints (hemorrhagic rectocolitis and Crohn's disease);
including cases in which an autoimmune component exists.

PHARMACEUTICAL SECTION

The products of the invention are administered in the form of compositions which are appropriate for the nature and severity of the complaint to be treated. The daily dose in humans is usually between 2 mg and 1 g of product, which may be taken in one or more individual doses. The compositions are prepared in forms which are compatible with the intended route of administration, such as, for example, tablets, coated tablets, capsules, mouthwashes, aerosols, powders for inhalation, suppositories, gels or suspensions. These compositions are prepared by methods which are familiar to those skilled in the art and comprise from 0.5 to 60% by weight of active principle (compound of formula I) and 40 to 99.5% by weight of a pharmaceutical vehicle which is appropriate and compatible with the active principle and the physical form of the intended composition. By way of example, the composition and the preparation of tablets containing a compound of the invention are given below:

| | |
|---|---|
| Active substance of formula (I) | 1 to 75 mg |
| Lactose | 124 to 74 mg |
| Microcrystalline cellulose | 36 to 60 mg |
| Polyvinylpyrrolidone | 6 mg |
| Sodium carboxymethyl starch | 8 mg |
| Magnesium stearate | 1 mg |

Mix together the active substance, the lactose, the microcrystalline cellulose and the carboxymethyl starch. Moisten and granulate using an aqueous or alcoholic polyvinylpyrrolidone solution of appropriate concentration. Dry and adjust the size distribution of the granule. Mix in the magnesium stearate homogeneously. Carry out tableting to give 200 mg per tablet.

We claim:

1. A compound of formula (1)

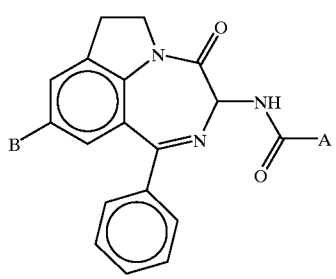

(I)

containing from one to four nitrogen atoms, each A optionally being substituted with one to three groups chosen independently from halogen, lower alkyl haloallyl lower alkoxy, cycloalkyloxy, amino, lower alkylcarbonylamino or lower alkyloxycarbonylamino;

B is:
1°) —$OR_1$, $R_1$ being —H or $R_4$,
2°) —$NR_aR_b$, $R_a$ being —C(NH)$NH_2$ and $R_b$ being —H,
3°) —$NR_cR_d$, $R_c$ being $R_4$ and $R_d$ being —H,
4°) —$NR_eR_f$, $R_e$ and $R_f$ independently being —H or lower alkyl, or
5°) —N—$R_2$—$R_3$, $R_2$ and $R_3$ forming, together with the nitrogen atom to which they are attached, a saturated five- to seven-membered heterocycle which may comprise, as second hetero atom not attached directly to the nitrogen atom, an oxygen, a sulfur or a nitrogen;

$R_4$ is:
1°) —$CH_2$—$CO_2H$
2°) —CO—$(CH_2)_p$—$CO_2H$,
3°) —CO—A, where A has the definition indicated above,
4°) —CO—CH=CH—$CO_2H$,
5°) —CO—$(CH_2)_n$—$CH_3$, n being an integer equal to or greater than 0 and less than or equal to 18,
6°) —CO—$(CH_2$—O—$CH_2)_p$—$CH_2$—O—$CH_3$,
7°) —CO—$(CH_2$—O—$CH_2)_p$—$CO_2H$,
8°) —$(CH_2)_p$—$NR_5R_6$, $R_5$ and $R_6$ independently being —H or lower alkyl or
9°) —$(CH_2)_p$—N—$R_5$—$R_6$, $R_5$ and $R_6$ forming, together with the nitrogen atom to which they are attached, a saturated five- to seven-membered heterocycle which may comprise, as second hetero atom not attached directly to the nitrogen atom, an oxygen, a sulfur or a nitrogen;

p is an integer equal to 2, 3 or 4; the racemic forms and isomers thereof of configuration determined in particular by carbon 3 of the diazepinoindol-4-one ring, as well as the pharmaceutically acceptable salts thereof.

2. A compound of formula (1) according to claim 1, characterized in that their absolute configuration is R according to the Cahn-Igold-Prelog rule, considering the asnmmetric carbon atom in an alpha position relative to the carbonyl of the diazepine ring.

3. A compound of formula (1) according to claim 1, characterized in that B is $OR_1$ or $NR_2R_3$ where $R_1R_2R_3$ are hydrogen.

4. A compound of formula (I) according to claim 1, in which A is aryl substituted with one to 3 groups independently chosen from halogen, amino and lower alkoxy.

5. A compound of formula (I) according to claim 1, in which A is monocyclic nitrogen-containing heteroaryl comprising from 1 to 2 nitrogen atoms or bicyclic nitrogen-containing heteroaryl comprising from 1 to 4 nitrogen atoms.

6. A compound of formula (1) according to claim 5, in which A is heteroaryl substituted with amino, lower alkyl, lower alkyloxycarbonylamino or alkylcarbonylamino groups.

7. A compound ofthe formula (II)

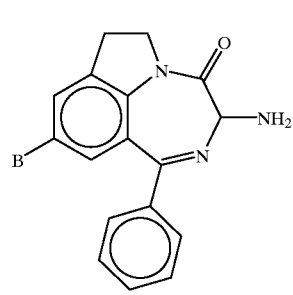

(II)

in which B is $OR_1$ or $NR_2R_3$, $R_1$, $R_2$ and $R_3$ being hydrogen.

8. Process for the preparation of the compounds (I)

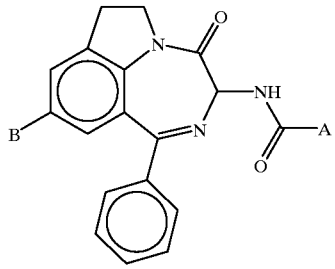

(I)

according to claim 1, characterized in that it consists:

a) In order to obtain the compounds (Ib) of formula (I) in which B is an —OH group:

in acylating an aminodiazepinoindole $(II_b)$ of formula (II), in which B is an —OH group, with a reactant (III) of formula Z—CO—A, in which A is nitrogen-containing aryl or heteroaryl, each optionally substituted with one to three groups independently chosen from halogen, lower alkyl, lower haloalkyl, lower alkoxy, cycloalkyloxy, amino, lower alkyloxycarbonylamino or lower alkylcarbonylamino, and Z represents a halogen, a hydroxyl group, an azido group, an imidazol-1-yl group or a group —O—CO—$Z_1$, it being possible for $Z_1$ to be, besides A, a bulky alkyl or alkoxy radical containing from 3 to 6 carbon atoms, or alternatively Z may be a group O—$Z_2$, $Z_2$ being an aromatic group containing one or two rings substituted with one or more nitro or halo radicals, or in O-demethylating, in position 9 of the diazepinoindole ring, an intermediate compound $(I'_c)$ of formula

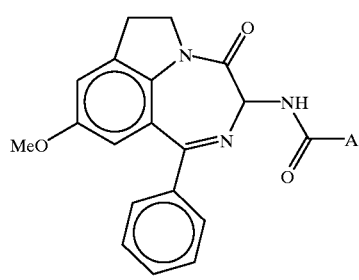

$(I'c)$ with a boron or aluminum halide, or in diazotizing, in a first step, a compound $(I_e)$ of formula (I), in which B is an —$NH_2$ group, and then in hydrolyzing, in a second step, the intermediate diazonium salt, and b) in order to obtain the compounds $(I_e)$ of the invention, of formula (I), in which B is an —$NH_2$ group, in acylating a compound $(II_e)$ of formula (II), in which B is an —$NH_2$ group, with the reactant (III) defined in a) of this claim, or in reducing the nitro radical of an intermediate compound $(I'_d)$ of formula

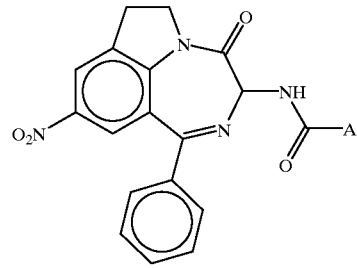

$(I'd)$ by the action of a metal such as Zn or Sn in acidic medium, or that of a metal chloride or sulfide such as $TiCi_3$ or $Na_2S$, and c) in order to obtain the compounds $(I_{bb})$ of the invention, of formula (I), in which B is a group —O—CO—V; V being a group chosen from:

A, as defined in a) of this claim, $(CH_2)_p$—$CO_2H$, where p is an integer equal to 2, 3 or 4,

CH=CH—$CO_2H$, $(CH_2)_n$—$CH_3$, where n is an integer equal to or greater than 0 and less than or equal to 18, $(CH_2$—O—$CH_2)_p$—$CH_2$—O—$CH_3$, where p is an integer equal to 2, 3 or 4, or $(CH_2$—O—$CH_2)_p$—$CO_2H$, where p is an integer equal to 2, 3 or 4, in esterifying a compound $(I_b)$ defined in a), with a reactant (III') of formula V—CO—Z, in which Z has the meaning defined in a) of this claim, and d) in order to obtain the compounds $(I_{bc})$ of the invention, of formula (I), in which B is a group —O—$R_4$, $R_4$ being a group chosen from:

—$CH_2$—$CO_2H$,

—$(CH_2)_p$—$NR_5R_6$, where $R_5$ and $R_6$ are independently —H or lower alkyl, or —$(CH_2)_p$—N—$R_5$—$R_6$, where $R_5$ and $R_6$ form, together with the nitrogen atom to which they are attached, a heterocycle, in reacting a compound $(I_b)$, defined in a), with a strong base such as an alkali metal hydride, in order to form a phenate, which is reacted with a halide $XR_4$, and e) in order to obtain the compounds $(I_{ea})$ of the invention, of formula (I), in which B is a group —NH—C (NH) —$NH_2$, in reacting a compound $(I_e)$, defined in b), with a guanylating agent such as cyanamide, and f) in order to obtain the compounds $(I_{eb})$ of the invention, of formula (I), in which B is a group —NH—CO—V, V having the meaning defined in c) of this claim, in amidating a compound $(I_e)$, defined in b), with the reactant (III'): V—CO—Z defined in c) of this claim, and g) in order to obtain the compounds $(I_{ec})$ of the invention, of formula (I), in which B is a group —NH—$R_2$, R being lower alkyl or a group $R_4$ as defined in d) of this claim, in reacting a compound (Ie) defined in b), in the presence of a strong base with an alkyl halide $XR_2$, and h) in order to obtain the compounds $(I_{ed})$ of the invention, of formula (I), in which B is a group —$NR_2R_3$, $R_2$ and $R_3$ being lower alkyls, in performing the reductive alkylation of a compound $(I_{ec})$, defined in g) of this claim, with an aldehyde $R'_3CHO$, in which $R'_3$ is the immediately lower homolog of $R_3$, and i) in order to obtain the compounds $(I_{ee})$ of the invention, of formula (I), in which B is a group —N—$R_2$—$R_3$, $R_2$ and $R_3$ forming a heterocycle, in carrying out a cyclization by reaction of a compound (I$_e$), defined in b), with a reactant of formula

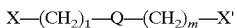

in which X and X', which may be the same or different, are halogens, Q is:
  a single valency bond, and 1 and m are integers ranging from 1 to 3 with l+m greater than or equal to 4 and less than or equal to 6,
  an oxygen, a sulfur or a group —NH—, in which case l and m are integers ranging from 1 to 3 with l+m greater than or equal to 3 and less than or equal to 5, or, in alkylating an intermediate diazepinoindole (II$_f$) of formula II wherein B is a group —N—R$_2$—R$_3$, R$_2$ and R$_3$ forming with the nitrogen atom a heterocycle, with a reactant (III) of formula Z—CO—A as previously defined.

9. A method for the treatment of inflammation in a subject which comprises administering to said subject a therapeutically effective amount of a diazepinoindole according to claim 1.

10. A method for the treatment of inflammation in a subject which comprises administering to said subject a therapeutically effective amount of a diazepinoindole according to claim 1.

11. The compound:
(3R)-Isoquinoline-3-carboxylic acid (9-hydroxy-4-oxo-1-phenyl-3,4,6,7-tetrahydro-[1,4]diazepino [6,7,1-hi]indol-3-yl) amide;
(3R)-4-t-Butyloxycarbonylamino-N-(9-amino-4-oxo-1-phenyl-3,4,6,7,-tetrahydro [1,4]diazepino [6,7,1-hi]indol 3-yl) benzamide;
(3R)-4-Amino-N-(9-amino-4-oxo-1-phenyl-3,4,6,7-tetrahydro [1,4]diazepino [6,7,1-hi]indol-3-yl) benzamide;
(3R)-4-Amino-N-(9-Amino-4-oxo-1-phenyl-3,4,6,7-tetrahydro [1,4]diazepino [6,7,1-hi]indol-3-yl)-3,5-dichlorobenzamide;
(3R)-4-Amino-N-[9-(4-amino-3,5-dichlorobenzamido)-4-oxo-1-phenyl-3,4,6,7-tetrahydro [1,4]-diazepino [6,7,1-hi]indol-3-yl]-3,5-dichlorobenzamide;
(3R)-2-Acetylamino-N-(9-amino-4-oxo-1-phenyl-3,4,6,7-tetrahydro [1,4]diazepino [6,7,1-hi]indol-3-yl) benzamide;
(3R) - N-(9-Amino-4-oxo-1-phenyl-3,4,6,7-tetrahydro [1,4] diazepino [6,7,1-hi]indol-3-yl)-2-methoxybenzamide;
(3R)-4-Amino-N-(9-amino-4-oxo-1-phenyl-3,4,6,7-tetrahydro [1,4]diazepino 6,7,1-hi]indol-3-yl)-5-chloro-2-methoxybenzamide;
(3R)-N-(9-Amino-4-oxo-1-phenyl-3,4,6,7-tetrahydro [1,4] diazepino [6,7,1-hi]indol-3-yl-3-cyclopentyloxy-4-methoxybenzamide;
(3R)-Pyridine-2-carboxylic acid (9-amino-4-oxo-1-phenyl-3,4,6,7-tetrahydro [1,4]diazepino [6,7,1-hi]indol-3-yl) amide;
(3R)-N-(9-Amino-4-oxo-1-phenyl-3,4,6,7-tetrahydro [1,4] diazepino [6,7,1,-hi]indol-3 -yl-isonicotinamide;
(3R)-3-t-Butyloxycarbonylamino-N-(9-amino-4-oxo-1-phenyl-3,4,6,7-tetrahydro [1,4 ]diazepino [6,7,1-hi]indol-3-yl) isonicotinamide;
(3R)-3-Amino-N-(9-amino-4-oxo-1-phenyl-3, 4, 6, 7-tetrahydro [1,4]diazepino [6,7,1-hi]indol-3-yl) isonicotinamide;
(3R)-3-Acetylamino-N-(9-acetylamino-4-oxo-1-phenyl-3,4, 6,7-tetrahydro [1,4]diazepino-[6,7,1-hi]indol-3-yl) isonicotinamide;

(3R) -N-(9-Amino-4-oxo-1-phenyl -3,4,6,7-tetrahydro [1,4] diazepino[6,7,1-hi]indol-3yl-)-3,5-dichloroisonicotinamide;
(3R)-Pyrazine-2-carboxylic acid (9-arnino-4-oxo -1-phenyl-3,4,6,7-tetrahydro [1,4]diazepino [6,7,1-hi]indol-3-yl) amide;
(3R)Isoquinoline-3-carboxylic acid (9-amino-4-oxo-1-phenyl-3,4,6,7-tetrahydro [1,4]-diazepino [6,7,1-hi]indol-3-yl) amide;
(3R)-Quinoline-3-carboxylic acid (9-amino-4-oxo-1-phenyl-3,4,6,7-tetrahydro [1,4]-diazepino [6,7,1-hi]indol-3-yl)amide;
(3R)-4,7-Dimethylpyrazolo [5,1-c][1,2,4]triazine-3-carboxylic acid (9-amino-4-oxo-1-phenyl-3,4,6,7-tetrahydro [1,4]diazepino [6,7,1-hi]indol-3-yl )amide;
(3R)-4-Amino-3,5-dichloro-N-(9-dirnethylamino-4-oxo-1-phenyl-3,4,6,7-tetrahydro [1,4]diazepino [6,7,1-hi]indol-3-yl) benzamnide;
(3R)-4-Amino-3,5-dichloro-N-(4-oxo-1-phenyl-9-pyrrolidin-1-yl-3,4,6,7-tetrahydro [1,4]-diazepino [6,7,1-hi]indol-3-yl)benzamide;
(3R)-4-Amino-3,5-dichloro-N-(4-oxo-1-phenyl-9-morpholin-1-yl-3,4,6,7-tetrahydro [1,4]diazepino [6,7,1-hi]indol-3-yl)benzamide;
(3R)-4-Amino-3,5-dichloro-N-(9-quanidino-4-oxo-1-phenyl-3,4,6,7-tetrahydro [1,4]-diazepino [6,7,1-hi]indol-3-yl)benzamide;
(3R)-N-(9-Acetylamino-4-oxo-1-phenyl-3,4,6,7-tetrahydro [1,4] diazepino [6,7,1-hi]indol-3-yl)-4-amino-3, 5-dichlorobenzamide;
(3R)-4-Amino-3,5-dichloro-N-(9-{2-[2-(2-methoxyethoxy) ethoxy]acetylamino}-4-oxo-1-phenyl-3,4,6,7-tetrahydro [1,4]diazepino-[6,7,1-hi]indol-3-yl)benzamide;
(3R)-(2-{2-[3-(4-Amino-3,5-dichlorobenzoyl-amnino)-4-oxo-1-phenyl-3,4,6,7-tetrahydro[1,4]diazepino [6,7,1-hi] indol-9-ylcarbamoyl-methoxy]ethoxy}ethoxy) acetic acid;
(3R)-Hexadecanoic acid [3-(4-amino-3,5-dichlorobenzoylamino)-4-oxo-1-phenyl-3,4,6,7-tetrahydro [1,4]diazepino[6,7,1-hi]indol-9-ylamide;
(3R)-Isoquinoline-3-carboxylic acid (9-acetylamino-4-oxo-1-phenyl-3,4,6,7-tetrahydro [1,4]diazepino [6,7,1-hi] indol-9-yl) amide;
(3R)N-(9-amino-4-oxo-1-phenyl-3,4,6,7-tetrahydro [1,4] diazepino [6,7,1-hi]indol-3-yl-2-benzofuranecarboxamide;
(3R)N-[4-oxo-1-phenyl-9-(pyrrolidin-1-yl)-3,4,6,7-tetrahydro [1,4]diazepino [6,7,1-hi]indol-3-yl)-isonicotinamide; or
(3R)-4,7-dimethyl-pyrazolo [5,1-c][1,2,4]triazine-3-carboxylic acid [4-oxo-1-pheny-9-(pyrrolidin-1-yl)-3,4,6, 7-tetrahydro [1,4]diazepino [6,7,1-hi]indol-3-yl-amide.

12. The compound:
(3R)-N-(9-amino-4-oxo-1-phenyl-3,4,6,7-tetrahydro [1,4 ]diazepino [6,7,1-hi]indol-3-yl) nicotinamide.

13. A pharmaceutical composition comprising a compound of claim 1 and a pharmaceutically acceptable carrier.

14. A pharmaceutical composition comprising a compound of claim 11 and a pharmaceutically acceptable carrier.

15. A pharmaceutical composition comprising a compound of claim 12 and a pharmaceutically acceptable carrier.

16. A method for the treatment of inflammation in a subject which comprises administering to said subject a therapeutically effective amount of a compound of claim 11.

17. A method for the treatment of inflammation in a subject which comprises administering to said subject a therapeutically effective amount of a compound of claim 12.

18. A method for the treatment of asthma in a subject which comprises administering to said subject a therapeutically effective amount of a compound of claim 1.

19. A method for the treatment of asthma in a subject which comprises administering to said subject a therapeutically effective amount of a compound of claim 11.

20. A method for the treatment of asthma in a subject which comprises administering to said subject a therapeutically effective amount of a compound of claim 12.

21. A method for the treatment of allergies in a subject which comprises administering to said subject a therapeutically effective amount of a compound of claim 1.

22. A method for the treatment of allergies in a subject which comprises administering to said subject a therapeutically effective amount of a compound of claim 11.

23. A method for the treatment of allergies in a subject which comprises administering to said subject a therapeutically effective amount of a compound of claim 12.

* * * * *

UNITED STATES PATENT AND TRADEMARK OFFICE
CERTIFICATE OF CORRECTION

PATENT NO.  : 5,972,927
DATED       : Oct. 26, 1999
INVENTOR(S) : Pascal et al.

Page 1 of 2

It is certified that error appears in the above-identified patent and that said Letters Patent is hereby corrected as shown below:

Column 41, line 39 "formula (1)" should read "formula (I)".
Column 41, line 55 insert "," between "alkyl" and "haloallyl".
Column 41, line 55 insert "," between "haloallyl" and "lower alkoxy".
Column 41, line 59 insert "— " before "B is".
Column 42, line 4 insert "— " before "R₄ is".
Column 42, line 17 insert "," between "alkyl" and "or".
Column 42, line 25 insert "— " before "p is".
Column 42, line 30 "formula (1)" should read "formula (I)".
Column 42, line 33 "asnmmetric" should read "asymmetric".
Column 42, line 35 "formula (1)" should read "formula (I)".
Column 42, line 48 "formula (1)" should read "formula (I)".
Column 42, line 52 "ofthe" should read "of the".
Column 43, line 19 "(Ib)" should read "($I_b$)".
Column 43, line 22 insert "— " before "in acylating".

UNITED STATES PATENT AND TRADEMARK OFFICE
CERTIFICATE OF CORRECTION

PATENT NO. : 5,972,927
DATED : October 26, 1999
INVENTOR(S) : Pascal et al

It is certified that error appears in the above-identified patent and that said Letters Patent is hereby corrected as shown below:

Column 43, line 38 insert "— " before "in O-demethylating".
Column 43, line 56 insert "— " before "in diazotizing".
Column 43, line 63 insert "— " before "in acylating".
Column 43, line 63 "of f ormula (II)" should read "of formula (II)".
Column 43, line 66 insert "— " before "in reducing".
Column 44, line 21 insert "— " before "A, as defined".
Column 44, line 22 insert "— " before "$(CH_2)_p-CO_2H$".
Column 44, line 23 insert "— " before "$CH = CH-CO_2H$".
Column 44, line 24 insert "— " before "$(CH_2)_n-CH_3$".
Column 44, line 26 insert "— " before "$(CH_2-O-CH_2)_p-CH_2-O-CH_3$".
Column 44, line 28 insert "— " before "$(CH_2-O-CH_2)_p-CO_2H$".
Column 45, line 8 insert "— " before " a single valency".
Column 45, line 11 insert "— " before "an oxygen".

Signed and Sealed this

Seventh Day of November, 2000

Q. TODD DICKINSON

*Attest:*

*Attesting Officer*   *Director of Patents and Trademarks*